(12) United States Patent
Xiong et al.

(10) Patent No.: US 11,571,403 B2
(45) Date of Patent: *Feb. 7, 2023

(54) METHODS FOR THE TREATMENT OF NON-ALCOHOLIC STEATOHEPATITIS

(71) Applicant: Eiger Biopharmaceuticals, Inc., Palo Alto, CA (US)

(72) Inventors: Xiaofeng Xiong, Santa Clara, CA (US); David A. Cory, Palo Alto, CA (US)

(73) Assignee: Eiger BioPharmaceuticals, Inc., Palo Alto, CA (US)

( * ) Notice: Subject to any disclaimer, the term of this patent is extended or adjusted under 35 U.S.C. 154(b) by 54 days.

This patent is subject to a terminal disclaimer.

(21) Appl. No.: 16/781,971

(22) Filed: Feb. 4, 2020

(65) Prior Publication Data

US 2020/0237696 A1  Jul. 30, 2020

Related U.S. Application Data

(63) Continuation of application No. 16/335,662, filed as application No. PCT/US2017/054087 on Sep. 28, 2017, now Pat. No. 10,588,880.

(60) Provisional application No. 62/469,722, filed on Mar. 10, 2017, provisional application No. 62/460,606, filed on Feb. 17, 2017, provisional application No. 62/400,963, filed on Sep. 28, 2016.

(51) Int. Cl.
| | | |
|---|---|---|
| *A61K 31/197* | (2006.01) | |
| *A61P 1/16* | (2006.01) | |
| *A61K 31/195* | (2006.01) | |
| *A61K 45/06* | (2006.01) | |
| *A61K 31/4184* | (2006.01) | |
| *A61P 29/00* | (2006.01) | |

(52) U.S. Cl.
CPC .......... *A61K 31/197* (2013.01); *A61K 31/195* (2013.01); *A61K 31/4184* (2013.01); *A61K 45/06* (2013.01); *A61P 1/16* (2018.01); *A61P 29/00* (2018.01)

(58) Field of Classification Search
CPC .... A61K 31/197; A61K 31/195; A61K 45/06; A61K 31/4184; A61P 1/16; A61P 29/00
USPC ........................................................ 514/394
See application file for complete search history.

(56) References Cited

U.S. PATENT DOCUMENTS

| | | | |
|---|---|---|---|
| 4,029,547 A | | 6/1977 | Umezawa et al. |
| 4,052,449 A | | 10/1977 | Umezawa et al. |
| 4,963,588 A | * | 10/1990 | Uzuka ............... A61P 7/06 514/563 |
| 6,245,813 B1 | * | 6/2001 | Zhou ............... A61P 31/12 514/563 |
| 9,233,089 B2 | | 1/2016 | Nicolls et al. |
| 2008/0025986 A1 | | 1/2008 | Ozes et al. |
| 2013/0251787 A1 | | 9/2013 | Nicolls et al. |
| 2013/0303548 A1 | | 11/2013 | Kashyap et al. |
| 2014/0066484 A1 | | 3/2014 | Bradford |
| 2015/0209314 A1 | | 7/2015 | Matsuda |
| 2016/0220586 A1 | * | 8/2016 | Andre ............... A61K 31/496 |
| 2017/0172954 A1 | | 6/2017 | Bisgaier et al. |
| 2019/0307714 A1 | | 10/2019 | Xiong et al. |

FOREIGN PATENT DOCUMENTS

| | | | |
|---|---|---|---|
| CN | 104784178 A | * 7/2015 | ............... A61K 9/45 |
| JP | H11-508247 A1 | 7/1999 | |
| JP | 2009-109426 A1 | 5/2009 | |
| JP | 2016-505613 A1 | 2/2016 | |
| WO | 2013-142369 A1 | 9/2013 | |
| WO | 2016-149126 A1 | 9/2016 | |
| WO | 2018-064373 A1 | 4/2018 | |
| WO | 2019-108551 A1 | 6/2019 | |

OTHER PUBLICATIONS

Hossain et al. Experimental Eye research, 2016, 149, 100-106 (Year: 2016).*
Translation of CN104784178A (Year: 2015).*
Duke, G. et al: "Fatty acid synthase inhibitor TVB-3664 reduces collagen accumulation in blemycin-induced murine skin fibrosis and reverses multiple components of diet-induced and biopsy-confirmed nonalcoholic steatohepatitis in mice treated with or without co-administered pirfenidone", Hepatology, vol. 66, Issue S1, Oct. 1, 2017, p. 1056A (Abstract 1994).
Komiya, C. et al: "Antifibrotic effect of pirfenidone in a mouse model of human nonalcoholic steatohepatitis", Scientific Reports, vol. 7, No. 1, Mar. 17, 2017, pp. 1-12, DOI: 10.1038/srep44754.
Toshihiro, S. et al: "Sensitive and early detection of mitochondrial dysfunction in the liver of NASH model mice by PET imaging with F-BCPP-BF", EJNMMI Research, vol. 8, No. 1, Jul. 16, 2018, pp. 1-8, DOI: 10.1186/S13550-018-0420-6.
Abd El-Kader, S.M.,. et al. "Non-Alcoholic Fatty Liver Disease: The Diagnosis and Management", World Journal of Hepatology, vol. 7, Issue 6, Apr. 28, 2015, p. 846-858, DOI:10.4254/wjh.v7.i6.846.
Arab, J.P., et al. "Serum Cytokeratin-18 Fragment Levels as Non-invasive Marker of Nonalcoholic Steatohepatitis in the Chilean Population." Gastroenterologia Y Hepatologia (English Edition), vol. 40, Issue 6, Jun.-Jul. 2017, p. 388-394, DOI:10.1016/j.gastrohep.2017.02.009. (English Abstract Attached).
Bedossa, P. et al. "Histopathological Algorithm and Scoring System for Evaluation of Liver Lesions in Morbidly Obese Patients", Hepatology, vol. 56, No. 5., Year 2012, p. 1751-1759, DOI:https://doi.org/10.1002/hep.25889.

(Continued)

*Primary Examiner* — Yevgeny Valenrod
(74) *Attorney, Agent, or Firm* — Kilpatrick Townsend & Stockton; Jennifer Giordano-Coltart; Rachna Ram

(57) ABSTRACT

In one aspect, methods of treating non-alcoholic steatohepatitis (NASH) or preventing or delaying the progression of non-alcoholic fatty liver disease (NAFLD) to NASH are provided. In some embodiments, the method comprises administering a therapeutically effective amount of ubenimex.

48 Claims, 2 Drawing Sheets

(56) References Cited

OTHER PUBLICATIONS

Bugianesi, E. et al. "How to Diagnose NAFLD in 2016", Journal of Hepatology, vol. 65, Issue 3, Sep. 2016. p. 643-644, DOI:https://doi.org/10.1016/j.jhep.2016.05.038.

Cassidy, S. et al. "Nonalcoholic Steatohepatitis (NASH) Drugs Market," Nature Reviews | Drug Discovery, vol. 15, Nov. 2016, p. 745-746, DOI:https://doi.org/10.1038/nrd.2016.188.

Castera, L., et al., "Noninvasive evaluation of NAFLD", Nat Rev Gastroenterol Hepatol., vol. 10, Issue 11, Year 2013, p. 666-675, DOI:10.1038/nrgastro.2013.175.

Feldstein, A.E., et al., "Cytokeratin-18 fragment levels as noninvasive biomarkers for nonalcoholic steatohepatitis: a multicenter validation study", Hepatology, vol. 50, Issue 4, Oct. 2009, p. 1072-1078, DOI:10.1002/hep.23050.

Folch, J., et al., "A simple method for the isolation and purification of total lipides from animal tissues", J Biol Chem., vol. 226, Issue 1, May 1, 1957, p. 497-509.

International Preliminary Report on Patentability dated Apr. 2, 2019 in International Patent Application No. PCT/US2017/054087, 11 pages.

International Search Report and Written Opinion dated Dec. 11, 2017 in International Patent Application No. PCT/US2017/054087, 11 pages.

Kleiner, D. et al. "Design and Validation of a Histological Scoring System for Nonalcoholic Fatty Liver Disease", Hepatology, vol. 41, No. 6, Year 2005, p. 1313-1321, DOI:https://doi.org/10.1002/hep.20701.

Musso, G. et al. "Non-Alcoholic Steatohepatitis: Emerging Molecular Targets and Therapeutic Strategies," Nature Reviews Drug Discovery, vol. 15, issue 4, Year 2016, p. 249-274, DOI:10.1038/nrd.2015.3.

Neuman, M.G., et al. "Biomarkers in Nonalcoholic Fatty Liver Disease", Canadian Journal of Gastroenterology and Hepatology, vol. 28, No. 11, December 201, p. 607-614, DOI:10.1155/2014/757929.

Rangwala, F., et al., "Increased Production of Sonic Hedgehog by Ballooned Hepatocytes", The Journal of Pathology, vol. 224, Issue 3, Year 2011, p. 401-410, DOI:10.1002/path.2888.

Saito, K., et al. "Characterization of Hepatic Lipid Profiles in a Mouse Model with Nonalcoholic Steatohepatitis and Subsequent Fibrosis", Scientific Reports, vol. 5, Article No. 12466, Aug. 20, 2015, 11 pages, DOI:https://doi.org/10.1038/srep12466.

Sanyal, A.J., et al. "Endpoints and Clinical Trial Design for Nonalcoholic Steatohepatitis", Hepatology, vol. 54, Issue 1, Year 2011, p. 344-353, DOI:https://doi.org/10.1002/hep.24376.

Schwimmer, J.B., et al., "Histopathology of Pediatric Nonalcoholic Fatty Liver Disease", Hepatology, vol. 42, Issue 3, Year 2005, p. 641-649, DOI:https://doi.org/10.1002/hep.20842.

Takahashi, S.I., et al., "The effects of bestatin, a microbial aminopeptidase inhibitor, on epidermal growth factor-induced DNA synthesis and cell division in primary cultured hepatocytes of rats", Experimental Cell Research, vol. 183, Issue 2, Aug. 1989, p. 399-412, DOI:https://doi.org/10.1016/0014-4827(89)90400-X.

Takahashi, Y., et al. "Histopathology of Nonalcoholic Fatty Liver Disease/Nonalcoholic Steatohepatitis", World Journal of Gastroenterology, vol. 20, Issue 42, Nov. 14, 2014, p. 15539-15548, DOI:10.3748/wjg.v20.i42.15539.

Toshiyama, R., et al., "Poly(ethylene glycol)-poly(lysine) block copolymer-ubenimex conjugate targets aminopeptidase N and exerts an antitumor effect in hepatocellular carcinoma stem cells", Oncogene, vol. 38, Issued 2019, p. 244-260, DOI:https://doi.org/10.1038/s41388-018-0406-x.

Yamashita, M., et al., "A CD13 inhibitor, ubenimex, synergistically enhances the effects of anticancer drugs in hepatocellular carcinoma", International Journal of Oncology, vol. 49, Issue 1, Year 2016, p. 89-98, DOI:10.3892/ijo.2016.3496.

Armendariz-Borunda, J., et al., "A pilot study in patients with established advanced liver fibrosis using pirfenidone", Gut, vol. 55, Issue 11, Nov. 2006, p. 1663-1665, DOI:10.1136/gut.2006.107136.

Flores-Contreras, L., et al., "Treatment with pirfenidone for two years decreases fibrosis, cytokine levels and enhances CB2 gene expression in patients with chronic hepatitis C", BMC Gastroenterology, vol. 14, Issue 131, (Year 2014), 11 pages. DOI:10.1186/1471-230X-14-131.

International Preliminary Report on Patentability dated Jun. 2, 2020 in International Patent Application No. PCT/US2018/062645, 11 pages.

International Search Report and Written Opinion dated Jan. 25, 2019 in International Patent Application No. PCT/US2018/062645, 14 pages.

Meng, H., et al., "Pirfenidone-loaded liposomes for lung targeting: preparation and in vitro/in vivo evaluation", Drug Design, Development and Therapy, vol. 9, Jun. 30, 2015, p. 3369-3376, DOI:10.2147/DDDT.S84046.

Shimada, M., et al., "Usefulness of a combined evaluation of the serum adiponectin level, HOMA-IR, and serum type IV collagen 7S level to predict the early stage of nonalcoholic steatohepatitis", The American Journal of Gastroenterology, vol. 102, Issue 9, (2007), p. 1931-1938.

Hu, C. et al., "Advances in studies on antitumor effects of ubenimex," China Pharmacy, vol. 24, No. 32, 2013, pp. 3061-3063, DOI: 10.6039/j.issn.1001-0408.2013.32.28.

Xu W., et al., "Progress on roles and mechanisms of farnesoid X receptor (FXR) in chronic liver diseases", Chinese Pharmacological Bulletin, vol. 26, No. 3, Mar. 2016, pp. 314-319, DOI: 10.3969/j.issn.1001-1978.2016.03.004.

* cited by examiner

METHODS FOR THE TREATMENT OF NON-ALCOHOLIC STEATOHEPATITIS

CROSS-REFERENCES TO RELATED APPLICATIONS

This application is a continuation of U.S. patent application Ser. No. 16/335,662, filed Mar. 21, 2019, which is a National Stage Entry of International Application No. PCT/US2017/054087, filed Sep. 28, 2017, which claims priority to U.S. Provisional Patent Application No. 62/400,963, filed Sep. 28, 2016; to U.S. Provisional Patent Application No. 62/460,606, filed Feb. 17, 2017; and to U.S. Provisional Patent Application No. 62/469,722 filed Mar. 10, 2017, the entire content of each of which is incorporated by reference herein for all purposes.

FIELD OF THE INVENTION

The present disclosure provides methods and compositions for the treatment of non-alcoholic steatohepatitis (NASH) and prevention of progression to fibrosis and cirrhosis of the liver and hepatocellular carcinoma (HCC) resulting therefrom, and so relates to the fields of medicine, medicinal chemistry, pharmacology, chemistry, and biology.

BACKGROUND OF THE INVENTION

Fatty liver, also known as fatty liver disease (FLD) or hepatic steatosis, is a reversible condition in which large vacuoles of triglyceride fat accumulate in liver cells via the process of steatosis (i.e., abnormal retention of lipids within a cell). Despite having multiple causes, fatty liver is most commonly associated with excessive alcohol consumption and obesity. FLD associated with other diseases that influence fat metabolism is referred to as "non-alcoholic" FLD or "NAFLD."

Fatty change represents the intracytoplasmatic accumulation of triglycerides (neutral fats). At the onset of FLD, the hepatocytes present small fat vacuoles (liposomes) around the nucleus (microvesicular fatty change). In late stages of FLD, the size of the vacuoles increase and vacuoles coalesce to produce irreversible fatty cysts or lesions. Liver disease with extensive inflammation and a high degree of steatosis often progresses to more severe forms of the disease.

Non-alcoholic steatohepatitis (NASH) is an extreme and progressive form of NAFLD that is not linked to alcohol consumption and is further accompanied by inflammation (hepatitis). NASH is accompanied by ballooning degeneration of hepatocytes (also referred to herein as "hepatocyte ballooning"), which refers to the increase in size (i.e., ballooning) of cells during this process that is considered to be a form of apoptosis. Ballooned cells are typically two to three times the size of adjacent hepatocytes and characterized by a wispy cleared cytoplasm on H&E stained sections. Liver cell death and the inflammatory response lead to activation of stellate cells, which play a pivotal role in hepatic fibrosis. Further disease progression leads to cirrhosis and hepatocellular carcinoma (HCC), resulting in liver failure and, ultimately, death.

For patients suffering from early stages of NASH, lifestyle intervention, such as significant weight reduction, may slow or even reverse the process of steatosis. However, for patients with advanced NASH, there are no currently available therapies. For example, a recent clinical study of cenicriviroc for the treatment of advanced NASH failed to meet its primary endpoint of improving inflammation and liver damage after a year of treatment. Given the severity of FLD and NASH and unmet clinical need, an effective therapeutic treatment is urgently needed.

BRIEF SUMMARY OF THE INVENTION

In one aspect, the present disclosure provides methods, materials, and pharmaceutical compositions, for treating and preventing the progression of FLD and NASH. It is envisaged that the methods and compositions described herein can slow or prevent NAFLD patients from progressing to NASH and can be used to treat NASH patients with beneficial effects of slowing, stopping, or reversing NASH disease progression in those patients In one aspect, the present disclosure relates to pharmaceutical compositions and methods for oral delivery of ubenimex ((2S)-2-[[(2S,3R)-3-amino-2-hydroxy-4-phenylbutanoyl]amino]-4-methylpentanoic acid; also known as N-[(2S,3R)-3-Amino-2-hydorxy-4-phenylbutyryl-L-leucine, or Bestatin™ as marketed by Nippon Kayaku in Japan) to treat FLD and NASH patients and to prevent and/or slow the progression of the disease to fibrosis, cirrhosis, HCC, and death. In many embodiments, these compositions for oral administration are formulated as immediate release preparations, e.g. tablets, capsules, or pills, and are conveniently packaged, for example, in the form of the pill bottles or blister packaging, for patients or their care providers to administer in therapeutically effective amounts.

In some embodiments, ubenimex is administered in the treatment of NASH in accordance with the disclosure by oral administration of doses ranging from as little as 5 mg per day to up to 500 mg per day at dosing frequencies of once (QD administration), twice (BID administration), or thrice per day (TID administration). In some embodiments, administration of doses of from about 30 mg to about 150 mg administered from once to thrice daily is efficacious in the treatment of the majority of FLD and NASH patients, although lower doses can be efficacious in some patients.

In some embodiments, a patient receives continuous daily dosing of ubenimex, with a patient taking a therapeutically effective dose at least once per day for an extended period of time. Measureable symptomatic improvement or a detectable slowing of disease progression may not occur until after several weeks or more of treatment. Clinical trials to demonstrate efficacy will likely run for at least 12 and more likely 48 weeks of treatment. Accordingly, patients may be treated for multiple consecutive days, weeks (e.g., at least 12, 24, 36, or 48 weeks), months (e.g., at least 4 or 6 months), or years, including for the rest of the patient's life.

In some embodiments, a patient is administered one or more additional medications in a combination therapy for at least some portion of the time they receive ubenimex therapy. Such additional medications include, without limitation, a farnesoid X receptor (FXR) agonist (including but not limiting to obeticholic acid); a peroxisome proliferator-activator receptor (PPAR) agonist, e.g., a PPAR-alpha agonist, a PPAR-beta/delta agonist, or a PPAR-gamma agonist (including but not limited to elafibranor); aramchol; a caspase inhibitor (including but not limited to emricasan); a galectin 3 inhibitor (including but not limited to GR-MD-02, Galectin Therapeutics); a MAPK5 inhibitor (including but not limited to GS-4997, Gilead Sciences); an FGF21 agonist (including but not limited to BMS-986036, Bristol-Myers Squibb); a LTD4 receptor antagonist (including but not limited to tipelukast); a niacin analog (including but not limited to ARI 3037MO, Arisaph Pharmaceuticals); an ASBT inhibitor (including but not limited to volixibat); an apoptosis signal regulating kinase 1 (ASK1) inhibitor; an angiotensin converting enzyme (ACE) inhibitor; an angiotensin receptor blocker (ARB, including but not limited to telmisartan); a chemokine receptor inhibitor (e.g. CCR2 and/or CCR5 inhibitors, including but not limited to cenicriviroc); a thiozolidinedione (including but not limited to rosiglitazone and pioglitazone); a GLP-1 analog (including but not limiting to semaglutide, liraglutide); and a biguanide (including but not limited to metformin). In some embodiments, such treatments in accordance with the disclosure can improve insulin sensitivity in adipose tissue by activating PPAR and generate biochemical and histological improvements in NASH.

In some embodiments, methods for treating NASH are provided, said methods comprising administration of ubenimex to a patient in need of treatment. In some embodiments, the ubenimex is administered orally. In some embodiments, the ubenimex is administered at a daily dosage of 1000 mg or less. In some embodiments, the daily dosage is from about 5 mg to approximately 450 mg. In some embodiments, the daily dosage is in the range of 5-450 mg and is administered QD, BID, or TID, wherein the daily dosage is administered using unit dosage forms comprising ubenimex in an amount of 5, 10, 15, 30, 60, 75, 90 or 150 mg. In some embodiments, the daily dosage is administered BID and each dose is administered at a dose of 250 mg, 240 mg, 225 mg, 210 mg, 200 mg, 180 mg, 150 mg, 125 mg, 120 mg, 100 mg, 90 mg, 75 mg, 60 mg, 50 mg, 30 mg, 15 mg, 10 mg, or 5 mg. In some embodiments, the daily dosage is administered TID and each dose is administered at a dose of 150 mg, 125 mg, 120 mg, 100 mg, 90 mg, 75 mg, 60 mg, 50 mg, 30 mg, 15 mg, 10 mg, or 5 mg. In some embodiments, the ubenimex is administered for at least 4 weeks. In some embodiments, treatment reduces fibrosis in the patient. In some embodiments, treatment reduces hepatocyte ballooning in the patient. In some embodiments, treatment reduces inflammation in the patient.

In some embodiments, methods for reducing hepatocyte ballooning in a NAFLD or NASH patient are provided, said method comprising administering ubenimex at a daily dosage of from 5 to 450 mg using consecutive daily dosing for at least 4 weeks. In some embodiments, the ubenimex is administered for at least 12 weeks.

In some embodiments, methods for decreasing inflammation and/or fibrosis in a NASH patient are provided, said method comprising administering ubenimex at a daily dosage of from 5 to 450 mg using consecutive daily dosing for at least 24 weeks. In some embodiments, the ubenimex is administered for at least 48 weeks.

In some embodiments, methods for the treatment or prevention of non-alcoholic steatohepatitis or its progression are provided, said method comprising administration of ubenimex and optionally a secondary pharmaceutical agent to a patient in need thereof. In some embodiments, the secondary pharmaceutical agent is a farnesoid X receptor (FXR) agonist, a peroxisome proliferator-activator receptor (PPAR) agonist, aramchol, a caspase inhibitor, a galectin 3 inhibitor, an FGF19 agonist, an FGF21 agonist, a LTD4 receptor antagonist, a niacin analog, an ASBT inhibitor, an apoptosis signal regulating kinase 1 (ASK1) inhibitor, an angiotensin converting enzyme (ACE) inhibitor, an angiotensin receptor blocker (ARB), a chemokine receptor inhibitor, a thiozolidinedione, a GLP-1 analog, a biguanide, or an NSAID. In some embodiments, the ubenimex is administered at a daily dosage of 1000 mg or less. In some embodiments, the ubenimex and the secondary pharmaceutical agent are administered for at least 4 weeks.

In another aspect, the disclosure also provides for the manufacture of a medicament for the treatment of NASH and/or for prevention of the progression of NAFLD to NASH, wherein the active ingredient in the medicament is ubenimex. In some embodiments, the medicament is a pharmaceutical composition comprising ubenimex and at least one pharmaceutically acceptable carrier. In various embodiments, the medicament is formulated for oral administration, including immediate release and sustained release pharmaceutical formulations. The disclosure also provides for the manufacture of unit dosage forms of the medicament useful in treating patients and pharmaceutical packs and kits comprising one or more containers with a solid or liquid formulation of ubenimex as described herein.

In some embodiments, pharmaceutical preparations comprising ubenimex for the treatment of non-alcoholic steatohepatitis are provided. In some embodiments, the pharmaceutical preparation is in the form of a tablet, capsule, or pill suitable for oral administration. In some embodiments, the pharmaceutical preparation comprises ubenimex in an amount ranging from about 5 mg to about 450 mg.

In another aspect, methods of treating non-alcoholic steatohepatitis (NASH) are provided, comprising administering to a subject in need of treatment a therapeutically effective amount of ubenimex. In some embodiments, the subject has early-stage or middle-stage NASH. In some embodiments, the ubenimex is administered at a total daily dose in the range of 5 mg to 1000 mg. In some embodiments, the ubenimex is administered at a daily dose of about 5 mg to about 450 mg. In some embodiments, the ubenimex is administered at a daily dose of about 20 mg to about 450 mg QD. In some embodiments, the ubenimex is administered at a daily dose of about 10 mg to about 200 mg BID. In some embodiments, the ubenimex is administered at a daily dose of about 10 mg to about 150 mg BID. In some embodiments, the ubenimex is administered for at least 4 weeks. In some embodiments, the ubenimex is administered for at least 12 weeks. In some embodiments, treatment results in a reduction in plasma CK-18 levels in the subject. In some embodiments, treatment results in a reduction in hepatocyte ballooning in the subject.

In some embodiments, the method of treating NASH comprises administering ubenimex in combination with a second therapeutic agent. In some embodiments, the second therapeutic agent is a farnesoid X receptor (FXR) agonist, a peroxisome proliferator-activator receptor (PPAR) agonist, aramchol, a caspase inhibitor, a galectin 3 inhibitor, a mitogen-activated protein kinase 5 (MAPK5) inhibitor, a fibroblast growth factor 19 (FGF19) agonist, a FGF21 agonist, a leukotriene D4 (LTD4) receptor antagonist, a niacin analog, an apical sodium bile acid cotransporter (ASBT) inhibitor, an apoptosis signal regulating kinase 1 (ASK1) inhibitor, an angiotensin converting enzyme (ACE) inhibitor, an angiotensin receptor blocker, a chemokine receptor inhibitor, a thiozolidinedione, a GLP-1 analog, a biguanide, or a non-steroidal anti-inflammatory drug (NSAID).

In another aspect, methods of delaying or preventing the progression of non-alcoholic fatty liver disease (NAFLD) to NASH in a subject having NAFLD are provided. In some embodiments, the method comprises administering to the subject a therapeutically effective amount of ubenimex. In some embodiments, treatment results in a reduction in hepatocyte ballooning in the subject. In some embodiments, the ubenimex is administered at a total daily dose in the range of 5 mg to 1000 mg. In some embodiments, the ubenimex is administered at a daily dose of about 5 mg to about 450 mg. In some embodiments, the ubenimex is administered at a daily dose of about 20 mg to about 450 mg QD. In some embodiments, the ubenimex is administered at a daily dose of about 10 mg to about 200 mg BID. In some embodiments, the ubenimex is administered at a daily dose of about 10 mg to about 150 mg BID. In some embodiments, the ubenimex is administered for at least 4 weeks. In some embodiments, the ubenimex is administered for at least 12 weeks.

In some embodiments, the method of delaying or preventing the progression of NAFLD to NASH comprises administering ubenimex in combination with a second therapeutic agent. In some embodiments, the second therapeutic agent is a farnesoid X receptor (FXR) agonist, a peroxisome proliferator-activator receptor (PPAR) agonist, aramchol, a caspase inhibitor, a galectin 3 inhibitor, a mitogen-activated protein kinase 5 (MAPK5) inhibitor, a fibroblast growth factor 19 (FGF19) agonist, a FGF21 agonist, a leukotriene D4 (LTD4) receptor antagonist, a niacin analog, an apical sodium bile acid cotransporter (ASBT) inhibitor, an apoptosis signal regulating kinase 1 (ASK1) inhibitor, an angiotensin converting enzyme (ACE) inhibitor, an angiotensin receptor blocker, a chemokine receptor inhibitor, a thiozolidinedione, a GLP-1 analog, a biguanide, or a non-steroidal anti-inflammatory drug (NSAID).

In still another aspect, methods of decreasing hepatocyte ballooning in a subject having NAFLD and/or NASH are provided. In some embodiments, the method comprises administering to the subject a therapeutically effective amount of ubenimex for at least 4 weeks. In some embodiments, the method comprises administering to the subject a therapeutically effective amount of ubenimex for at least 12 weeks. In some embodiments, the subject has NAFLD. In some embodiments, the subject has NASH.

In yet another aspect, methods of decreasing inflammation in a subject having NAFLD and/or NASH are provided. In some embodiments, the method comprises administering to the subject a therapeutically effective amount of ubenimex for at least 24 weeks. In some embodiments, the method comprises administering to the subject a therapeutically effective amount of ubenimex for at least 48 weeks. In some embodiments, the subject has NAFLD. In some embodiments, the subject has NASH.

In yet another aspect, methods of decreasing fibrosis in a subject having NASH are provided. In some embodiments, the method comprises administering to the subject a therapeutically effective amount of ubenimex for at least 24 weeks. In some embodiments, the method comprises administering to the subject a therapeutically effective amount of ubenimex for at least 48 weeks.

In yet another aspect, pharmaceutical packages comprising unit dosage forms of ubenimex and further comprising unit dosage forms of a second therapeutic agent are provided. In some embodiments, the second therapeutic agent is a FXR agonist, a PPAR agonist, aramchol, a caspase inhibitor, a galectin 3 inhibitor, a MAPK5 inhibitor, a FGF19 agonist, a FGF21 agonist, a LTD4 receptor antagonist, a niacin analog, an ASBT inhibitor, an ASK1 inhibitor, an ACE inhibitor, an angiotensin receptor blocker, a chemokine receptor inhibitor, a thiozolidinedione, a GLP-1 analog, a biguanide, or an NSAID. In some embodiments, the second therapeutic agent is not a chemotherapy agent. In some embodiments, each unit dosage form of ubenimex comprises ubenimex in an amount from 5 mg to 1000 mg. In some embodiments, each unit dosage form of ubenimex comprises ubenimex in an amount from about 5 mg to about 450 mg. In some embodiments, the ubenimex is formulated for immediate release. In some embodiments, the ubenimex is formulated for controlled release. In some embodiments, the ubenimex is in the form of a tablet, a capsule, or a pill.

DETAILED DESCRIPTION OF THE INVENTION

I. Introduction

Figure 1A:
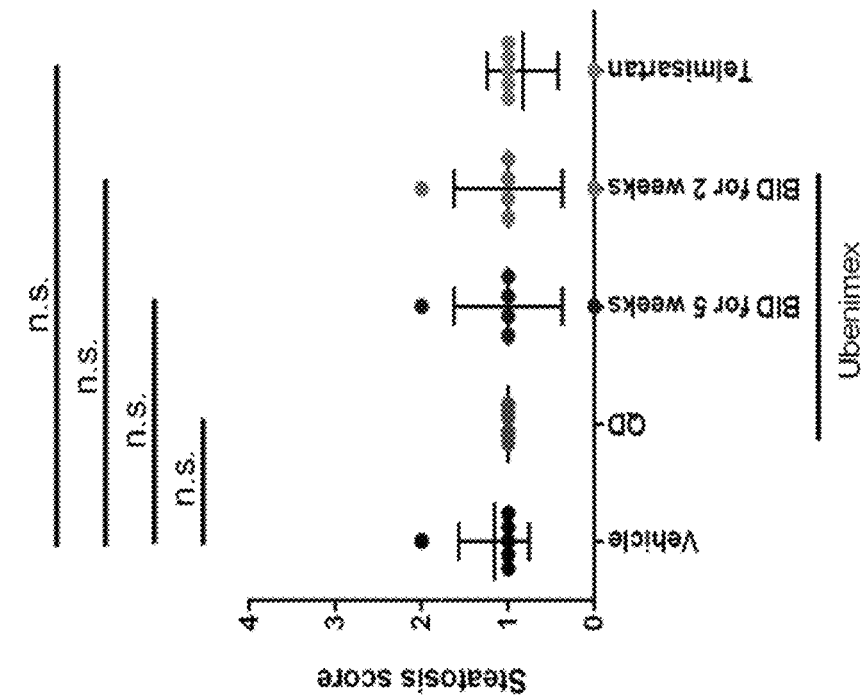
FIG. 1A-1D. NAFLD activity score and component scores in mice treated with vehicle, ubenimex QD for 5 weeks, ubenimex BID for 5 weeks, ubenimex BID for 2 weeks, or telmisartan for 5 weeks. (A) NAFLD activity scores for the five groups. (B) Steatosis component scores for the five groups. (C) Inflammation component scores for the five groups. (D) Hepatocyte ballooning component scores for the five groups.

Nonalcoholic fatty liver disease (NAFLD) is a spectrum of liver disease that ranges from simple steatosis to nonalcoholic steatohepatitis (NASH), fibrosis, and cirrhosis. The key histological features of NASH include steatosis, hepatocyte ballooning, and lobular inflammation, and fibrosis is also typically observed. Takahashi et al., *World J Gastroenterol*, 2014, 20:15539-15548.

As described in the Examples section below, it has been found that in an animal model of NASH, ubenimex demonstrated efficacy in slowing and preventing hepatocyte ballooning and reduced steatosis and lobular inflammation after only three weeks of dosing. Accordingly, in one aspect, methods of treating one or more symptoms of NAFLD and/or NASH, such as hepatocyte ballooning, steatosis, and lobular inflammation, are provided. Furthermore, Example 1 describes that plasma CK-18 levels declined significantly relative to those measured in control animals. Thus, in some embodiments, administration of ubenimex as described herein decreases ballooning and measurably lowers plasma and/or liver CK-18 levels in as few as 3 to 12 weeks after treatment initiation. In some embodiments, continued daily administration of ubenimex is efficacious in decreasing inflammation and fibrosis in NASH within 24 to 48 weeks after treatment initiation. In some embodiments, treatment with ubenimex results in an improvement in one or more parameters such as improved ALT enzyme levels, decreased inflammation, decreased steatosis, reduced severity of NASH symptoms, reduced levels of NASH biomarkers such as CK-18, or the slowing, stopping, or reversing of liver fibrosis.

II. Definitions

The terminology used herein is for the purpose of describing particular embodiments only and is not intended to be limiting. In this specification and in the claims that follow, reference will be made to a number of terms, which shall be defined to have the definitions set forth below. Unless otherwise defined, all technical and scientific terms used herein have the same meaning as commonly understood by one of ordinary skill in the art to which this invention belongs. The singular forms also include the plural unless the context clearly dictates otherwise. Thus, the singular forms "a," "an," and "the" include plural referents unless the context clearly dictates otherwise.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

Acronyms. The following acronyms are used throughout the specification and defined as follows: NASH: non-alcoholic steatohepatitis; NAFLD: non-alcoholic fatty liver disease; QD: one a day; BID: twice a day; TID: three times a day.

As used herein, "active agent" refers to a compound or drug that exerts a preventative or therapeutic effect on a disease or condition. As used herein, "active agent" can refer to either a single active agent or to a combination of two or more different active agents.

The terms "administer" and "administration" refer to a method of delivering a compound, a composition, or an agent to the desired site of biological action. These methods include, but are not limited to, oral delivery, intravenous delivery, parenteral delivery, intramuscular delivery, intraperitoneal delivery, or subcutaneous delivery.

As used herein, "capsules" are unit dosage forms (e.g., for oral administration) in which the active agent-containing composition may be encapsulated in the form of a liquid or solid (including particulates such as granules, beads, powders or pellets). Suitable capsules may be either hard or soft, and are typically made of gelatin, starch, or a cellulosic material. In some embodiments, the capsules are gelatin capsules.

The term "compound" refers to a molecule and encompasses not only the specified molecular entity but, if the compound is an active agent or drug, also its pharmaceutically acceptable, pharmacologically active analogs, including, but not limited to, active metabolites, amides, conjugates, esters, hydrates, polymorphs, prodrugs, salts, solvates, and other such derivatives, analogs, including deuterated analogs and analogs containing radioactive atoms or other labeling moieties, and related compounds.

The term "comprising" is intended to mean that the compounds, compositions and methods include the recited elements, but not excluding others. "Consisting essentially of," when used to define compounds, compositions and methods, means excluding other elements that would materially affect the basic and novel characteristics of the claimed invention. "Consisting of" means excluding any element, step, or ingredient not specified in the claim. Embodiments defined by each of these transition terms are within the scope of this invention.

The term "CK-18" refers to cytokeratin-18 fragment, which has been identified as a noninvasive biomarker for NASH in that it is markedly increased in patients with NASH as determined by histology and higher blood plasma levels of the fragment correlate with the odds of having fibrosis on liver biopsy. See, Feldstein et al., *Hepatology*, 2009, 50:1072-8, incorporated by reference herein.

The term "dosage form" refers to a form of a pharmaceutical composition for administration to a subject (e.g., a human or non-human animal having a disease or condition to be treated). "Dose" refers to an amount of active agent. "Unit dosage form" refers to a dosage form that contains a fixed amount of active agent. For example, a single tablet or capsule is a unit dosage form. In some embodiments, multiple unit dosage forms are administered to provide a therapeutically effective dose.

The term "oral unit dosage form," as used herein, refers to a unit dosage form that is intended to be orally administered.

The terms "effective amount" and "therapeutically effective amount" refer to an amount of an active agent being administered that will treat to some extent a disease, disorder, or condition, e.g., relieve one or more of the symptoms of the disease being treated (e.g., NASH), and/or that amount that will prevent, to some extent, one or more of the symptoms of the disease that the subject being treated has or is at risk of developing. For example, for a given parameter, a therapeutically effective amount will show an increase or decrease of therapeutic effect of at least 5%, 10%, 15%, 20%, 25%, 30%, 40%, 50%, 60%, 70%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control.

An "excipient" or "carrier," as used herein, refers to a biologically inactive substance used in combination with an active agent(s) of the formulation. An excipient can be used, for example, as a solubilizing agent, a stabilizing agent, a diluent, an inert carrier, a preservative, a binder, a disintegrant, a coating agent, a flavoring agent, or a coloring agent. A wide variety of pharmaceutically acceptable excipients, such as vehicles, adjuvants, carriers or diluents, and auxiliary substances, such as pH adjusting and buffering agents, tonicity adjusting agents, stabilizers, wetting agents and the like, are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The term "parenteral administration," as used herein, refers to a non-oral means of administration, and includes subcutaneous, intravenous, and intramuscular routes of administration.

The term "pharmaceutical composition" refers to a composition that is suitable for administration to a subject. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, inhalational, and the like.

The term "pharmaceutically acceptable," as used with reference to a compound or component, means that the compound or component is generally safe, non-toxic, and not biologically undesirable. When the term "pharmaceutically acceptable" is used herein to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

The term "pharmaceutically acceptable salt" refers to a derivative of an active agent produced by making acid or base salts thereof. Examples of pharmaceutically acceptable salts include, but are not limited to, mineral or organic acid salts of basic residues such as amines, alkali or organic salts of acidic residues such as carboxylic acids, and the like. Pharmaceutically acceptable salts include the conventional non-toxic salts or the quaternary ammonium salts of the parent compound formed, for example, from non-toxic inorganic or organic acids. Pharmaceutically acceptable salts include those formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Pharmaceutically acceptable salts include solvent addition forms (solvates) or crystal forms (polymorphs) as defined herein, of the same salt.

The terms "prevention," "preventing," and "prevent" mean avoiding the onset of a clinically evident disease progression altogether or slowing the onset of a pre-clinically evident stage of a disease in individuals at risk. Prevention includes prophylactic treatment of those at risk of developing a disease.

The term "sign," as used herein, means an indication of disease and includes conditions that can be observed by a doctor, nurse, or other health care professional.

The terms "subject" and "patient" interchangeably refer to a human or non-human animal (e.g., mammal) suitable for treatment with an active agent. A subject in need thereof may have a disease (e.g., NASH) or may be at an increased risk, relative to the general population, of developing a disease (e.g., NASH). In some embodiments, a subject has been diagnosed with a disease (e.g., NASH).

The term "symptom" means a sign or other indication of disease, illness, or injury. Symptoms may be felt or noticed by the individual experiencing them or by others, including by non-health-care professionals.

The terms "treatment," "treating," and "treat" refer to any indicia of success in the treatment or amelioration of an injury, disease, or condition, including any objective or subjective parameter such as abatement, remission, improvement in patient survival, increase in survival time or rate, diminishing of symptoms or making the injury, disease, or condition more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

"Ubenimex" refers to (2S)-2-[[(2S,3R)-3-amino-2-hydroxy-4-phenylbutanoyl]amino]-4-methylpentanoic acid, which is also known as N-[(2S,3R)-3-Amino-2-hydorxy-4-phenylbutyryl-L-leucine, the structure of which is shown below:

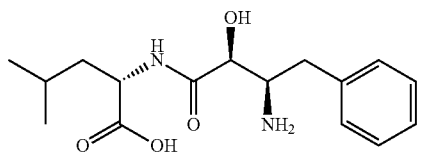 [SMILES: CC(C)C[C@H](NC(=O)[C@@H](O)[C@H](N)Cc1ccccc1)C(=O)O]

Ubenimex is a zwitterionic molecule that has a solubility of 1.27 mg/mL in water and has a melting point of approximately 251° C. Ubenimex is described in U.S. Pat. Nos. 4,029,547 and 4,052,449, incorporated by reference herein. Reference herein to ubenimex also includes a reference to a pharmaceutically acceptable salt of ubenimex unless otherwise indicated or clear from context. In some embodiments, ubenimex is in the form of ubenimex hydrochloride. Ubenimex and pharmaceutically acceptable salts thereof are commercially available (e.g., Tocris Bioscience). Ubenimex can also be prepared according to methods known in the art. See, e.g., U.S. Pat. No. 4,029,547, incorporated by reference herein.

All percentages are % w/w, unless otherwise specified. Unless otherwise indicated, "% weight" is percent weight of the specified component compared to total weight of the unit dosage (e.g., tablet or capsule). It will be appreciated that due to rounding or practical limits on quantitative measurements, reference to a quantity of API or excipient in a dosage form can include some variation, such as ±0.10% or ±0.5%.

III. Methods of Treating NAFLD and NASH

In one aspect, the present disclosure provides a therapy for the treatment of NASH that comprises administering to a patient in need of treatment a therapeutically efficacious dose of ubenimex. In some embodiments, the patient in need of treatment is a patient who has been diagnosed with NASH. In some embodiments, treatment with ubenimex as described herein slows, stops, or reverses NASH disease progression.

In another aspect, the present disclosure provides a therapy for the prevention of NASH or for slowing the progression of NAFLD to NASH by administering to a patient in need of treatment a therapeutically efficacious dose of ubenimex. In some embodiments, the patient in need of treatment is a patient who has been diagnosed with NAFLD.

Patient Population

Patients likely to benefit from the therapies of the present disclosure can be readily identified by a variety of means discussed herein or known to those of skill in the art. In addition, methods for determining whether a patient is responding to this therapy are also provided. In some embodiments, abdominal imaging tests, including ultrasound examination, computerized tomography (CT), and/or magnetic resonance imaging (MRI) can be used to diagnose patients with the disease, e.g. evaluate whether the disease is present and its severity. Such a non-invasive diagnosis can be more definitively confirmed by liver biopsy, if desired. In some embodiments, one or more biomarkers is used to diagnose NAFLD or NASH. In some embodiments, a patient to be treated in accordance with the present disclosure has received a primary diagnosis of NASH or NAFLD and is not being treated with ubenimex for any other condition for which it is currently indicated or in clinical development (e.g., certain cancer patients, PAH indication, or lymphedema indication).

NAFLD is characterized by significant lipid deposition in hepatocytes and is typically defined as either excessive fat accumulation in the liver (with more than 5% of hepatocytes containing visible intracellular triglycerides) or steatosis affecting at least 5% of the liver volume or weight. El-Kader et al., *World J Hepatol*, 2015, 7:846-858. In some embodiments, a patient to be treated has NAFLD. Some patients also exhibit abnormal liver function, e.g., as determined by the presence of elevated serum aspartate aminotransferase (ALT), gamma glutamyl transpeptidase, or alkaline phosphatase levels. In some embodiments, a patient to be treated has NAFLD and further has an elevated ALT level, an elevated gamma glutamyl transpeptidase, or an elevated alkaline phosphatase level (e.g., a level that is about 1.5- to 4-fold above the upper limit of normal). In some embodiments, a patient to be treated has NAFLD and has an ALT level, gamma glutamyl transpeptidase level, or alkaline phosphatase level that is within the upper limit of normal.

In some embodiments, NAFLD is diagnosed using an imaging test. In some embodiments, NAFLD is diagnosed using a scoring system such as but not limited to fatty liver index (in which a score >60 indicates a high risk for NAFLD), NAFLD liver fat score, NAFLD activity score, or hepatic steatosis index. In some embodiments, NAFLD is diagnosed using a NAFLD activity score (NAS), which provides a composite score based on the degree of steatosis (0-3), lobular inflammation (0-3), and hepatocyte ballooning (0-2). See, Kleiner et al., *Hepatology*, 2005, 41:1313-1321; Bugianesi et al., J Hepatology, 2016, 65:643-644.

NASH has been classified pathologically into type 1 and type 2 forms, of which the type 1 form is more commonly found in adult patients, while the type 2 form is more commonly found in children. Type 1 NASH is typically characterized by steatosis, hepatocyte ballooning, and perisinusoidal fibrosis. Type 2 NASH is typically characterized by steatosis, portal inflammation, and portal fibrosis. See, e.g., Schwimmer et al., *Hepatology*, 2005, 42:641-649. Further progression of NASH can lead to severe fibrosis, cirrhosis, and end-stage liver disease. In some embodiments, a patient to be treated has Type 1 NASH. In some embodiments, a patient to be treated has Type 2 NASH. In some embodiments, a patient to be treated has early-stage NASH. In some embodiments, a patient to be treated has middle-stage NASH. In some embodiments, a patient to be treated has late-stage NASH (e.g., has severe fibrosis and/or cirrhosis of the liver).

In some embodiments, NASH is diagnosed using an imaging test. In some embodiments, NASH is diagnosed using a scoring system such as but not limited to NAFLD activity score (e.g., a score of 5) or a steatosis, activity, and fibrosis (SAF) score, or a NAFLD fibrosis score; a serum biomarker (e.g., cytokeratin-18); or a combination thereof. See, Bedossa et al., *Hepatology*, 2012, 56:1751-1759; Arab et al., *Gastroenterol Hepatol*, 2017, 40:388-394. In some embodiments, fibrosis is detected and/or measured using elastography (e.g., Fibroscan®).

In some embodiments, a patient to be treated is identified by use of one or more biomarkers such as CK-18. CK-18 levels, whether measured by immunohistochemistry, histology from liver biopsies, or via measurement of plasma levels in patients or individuals suspected of being at risk for the disease, will typically be elevated, relative to the levels measured in healthy individuals, in subjects in need of treatment. While the invention is not to be limited to a particular or any proposed mechanism of action, decreased CK-18 levels in NASH patients would be expected to correlate with decreased liver cell apoptosis. Accordingly, patients with NAFLD or NASH who are treated with ubenimex in accordance with the present disclosure should benefit from decreased liver cell apoptosis, relative to receiving no treatment or standard of care.

In some embodiments, a patient to be treated is a human adult. In some embodiments, a patient to be treated is a human child under 18 years of age (e.g., from age 2 to age 17).

In some embodiments, a patient to be treated does not have cancer. In some embodiments, a patient to be treated does not have acute non-lymphocytic leukemia. In some embodiments, a patient to be treated does not have lymphedema. In some embodiments, a patient to be treated does not have pulmonary arterial hypertension.

Dosage Regimen

In some embodiments, ubenimex is administered at a total daily dose that is about 1000 mg or less (e.g., less than 900 mg, less than 800 mg, less than 750 mg, less than 700 mg, less than 600 mg, or less than 500 mg). As used herein, the dose amount refers to the amount of active ingredient administered per dose, not the amount of the pharmaceutical formulation. In some embodiments, ubenimex is administered at a total daily dose in the range of about 5 mg to about 450 mg, e.g., from about 10 mg to about 450 mg, from about 20 mg to about 450 mg, from about 30 mg to about 450 mg, from about 10 mg to about 350 mg, from about 20 mg to about 350 mg, from about 30 mg to about 350 mg, from about 10 mg to about 250 mg, from about 20 mg to about 250 mg, or from about 30 mg to about 250 mg. This daily dose may be administered all at once: one time daily, although in some embodiments the once daily dose (QD administration) will be at least 30 mg or more. For BID administration, in some embodiments the daily dose will be 10-450 mg, e.g. 5-225 mg two times daily, although in some embodiments the dose will be at least 15 mg or more for BID administration. For TID administration, in some embodiments the daily dose will be 15-450 mg, e.g. 5-150 mg three times daily, although in some embodiments the dose will be at least 10 mg or more for TID administration. In some embodiments, ubenimex is administered at a daily dose of at least 20 mg, at least 30 mg, at least 40 mg, or at least 50 mg. In some embodiments, ubenimex is administered at a daily dose of about 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, or 450 mg.

In some embodiments, ubenimex is administered at a dosage of about 10 mg to 450 mg QD, e.g., about 15 mg to 400 mg QD, about 20 mg to about 350 mg QD, about 20 mg to about 300 mg QD, about 25 mg to about 250 mg QD, or about 25 mg to about 200 mg QD. In some embodiments, ubenimex is administered at dosage of about 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, or 450 mg QD.

In some embodiments, ubenimex is administered at a dosage of about 10 mg to 200 mg BID, e.g., about 20 mg to about 150 mg BID, about 20 mg to about 100 mg BID, or about 25 mg to about 150 mg BID. In some embodiments, ubenimex is administered at dosage of about 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg BID.

In some embodiments, ubenimex is administered at a dosage of about 10 mg to 150 mg TID, e.g., about 20 mg to about 150 mg TID, about 20 mg to about 100 mg TID, or about 25 mg to about 150 mg TID. In some embodiments, ubenimex is administered at dosage of about 20 mg, 25 mg, 30 mg, 40 mg, 50 mg, 60 mg, 70 mg, 80 mg, 90 mg, 100 mg, 110 mg, 120 mg, 130 mg, 140 mg, or 150 mg TID.

Formulations and unit dosage forms of ubenimex are further disclosed in Section IV below. In some embodiments, ubenimex is administered orally. In some embodiments, ubenimex is administered orally in a therapeutically effective dose at least once and no more than thrice daily on consecutive days for at least a week and typically longer.

In some embodiments, ubenimex is administered alone (i.e., not in combination with another medication) for part or all of the treatment period. In some embodiments, ubenimex is administered in combination with one or more other drugs, such as but not limited to a farnesoid X receptor (FXR) agonist (including but not limiting to obeticholic acid); a peroxisome proliferator-activator receptor (PPAR) agonist, e.g., a PPAR-alpha agonist, a PPAR-beta/delta agonist, or a PPAR-gamma agonist (including but not limited to elafibranor); aramchol; a caspase inhibitor (including but not limited to emricasan); a galectin 3 inhibitor (including but not limited to GR-MD-02, Galectin Therapeutics); a MAPK5 inhibitor (including but not limited to GS-4997, Gilead Sciences); an FGF21 agonist (including but not limited to BMS-986036, Bristol-Myers Squibb); a LTD4 receptor antagonist (including but not limited to tipelukast); a niacin analog (including but not limited to ARI 3037MO, Arisaph Pharmaceuticals); an ASBT inhibitor (including but not limited to volixibat); an apoptosis signal regulating kinase 1 (ASK1) inhibitor; an ACE inhibitor or ARBs (including telmisartan); a CCR2 and/or CCR5 inhibitor (including cenicriviroc); a thiazolidinedione (including rosiglitazone and pioglitazone); a GLP-1 analog (including but not limiting to semaglutide, liraglutide); or a biguanide such as metformin. Without being bound to a particular theory, it is believe that such treatments in accordance with the disclosure can improve insulin sensitivity in adipose tissue by activating PPAR and generate biochemical and histological improvements in NASH. Combination therapy with ubenimex and a second therapeutic agent is also disclosed in Section V below.

In some embodiments, ubenimex is administered as a pharmaceutical formulation suitable for oral, intranasal, rectal, topical, intraperitoneal, intravenous, intramuscular, subcutaneous, subdermal, transdermal, or intrathecal administration. In some embodiments, pharmaceutical formulations for use according to the present disclosure are prepared for oral administration and in an immediate release form suitable for QD, BID, or TID administration, and the dosage regimen is selected within the ranges provided herein in accordance with a variety of factors including type, species, age, weight, sex and medical condition of the patient; the severity of the condition to be treated; the route of administration; the renal and hepatic function of the patient; and the particular formulation employed. An ordinarily skilled physician or veterinarian can readily determine and prescribe the effective amount of the drug required to prevent, counter or arrest the progress of the condition in view of the teachings herein.

Duration of Treatment, Treatment Endpoints, and Monitoring Efficacy

In some embodiments, treatment with ubenimex (and optionally a second therapeutic agent) is administered for a predetermined time, an indefinite time, or until an endpoint is reached. In some embodiments, treatment is for at least 30 days or one month, at least 60 days or two months, at least 90 days or three months, at least 120 days or four months, at least 150 days or five months, or at least 180 days or six months. In some embodiments, treatment is continued for at least six months to one year. In some embodiments, ubenimex is administered (e.g., by consecutive daily administration of ubenimex as described herein) for at least a month, for at least 3 months, or for at least 6 months to at least a year. In other embodiments, treatment is continued for the rest of the patient's life or until administration is no longer effective in providing a meaningful therapeutic benefit. In some embodiments, treatment is administered on a continuous daily basis. In some embodiments, treatment is administered on a near continuous daily basis (e.g., ubenimex treatment is administered to a patient daily but the patient may occasionally miss a day of treatment).

In some embodiments, generally continuous (or near continuous) daily dosing is continued until treatment appears to no longer have a beneficial effect or until unacceptable side effects appear. Many patients will take the medication for at least a week, at least a month, and at least a year or longer. In some instances, a patient will take the medication from approximately 6 months to approximately 1 year. In some instances, a patient will take the medication for greater than 1 year. Many patients will take the medication for the rest of their lives.

In some embodiments, treatment according to the methods described herein results in an improvement in one or more parameters such as, but not limited to, an improvement in NAS (ballooning and inflammation) and/or fibrosis; an improvement in SAF (steatosis, activity, and fibrosis) score; complete resolution of steatohepatitis; no worsening of fibrosis; an improvement in fibrosis without a worsening of steatohepatitis; or an increased time to disease progression as measured by histopathologic assessment of progression to cirrhosis, death, liver transplant, hepatocellular carcinoma, and decompensation events such as hepatic encephalopathy, variceal bleeding requiring hospitalization, ascites requiring intervention, and spontaneous bacteria peritonitis. In some embodiments, treatment according to the methods described herein results in an improvement (i.e., a reduction) in hepatocyte ballooning. In some embodiments, hepatocyte ballooning is visualized using hematoxylin and eosin straining.

In some embodiments, treatment according to the methods described herein results in an improvement in one or more biomarkers of NAFLD or NASH, such as but not limited to markers of apoptosis (e.g., cytokeratin 18 (CK-18) fragments), adipokines (e.g., adiponectin, leptin, resistin, or visfatin), inflammatory markers (e.g., TNF-α, IL-6, chemoattractant protein-1, or high sensitivity C-reactive protein). See, e.g., Neuman et al., *Can J Gastroenterol Hepatol*, 2014, 28:607-618; Castera et al., *Nat Rev Gastroenterol Hepatol.*, 2013, 10:666-675. In some embodiments, biomarker values are measured using a sample that comprises a fluid, e.g., blood, plasma, serum, urine, or cerebrospinal fluid. In some embodiments, biomarker values are measured using a sample that comprises cells and/or tissues, e.g., hepatocytes or liver tissue. In some embodiments, treatment results in an improvement in the biomarker CK-18. In some embodiments, treatment results in a reduction in plasma CK-18 levels in the subject.

In some embodiments, a patient is monitored during the course of ubenimex therapy using a diagnostic test as described herein (e.g., using abdominal imaging tests). In some embodiments, the method further comprises continuing a course of therapy (e.g., a dosage of ubenimex as described herein). In some embodiments, the method further comprises tapering, reducing, or stopping the administered amount of ubenimex if the diagnosis warrants, e.g. when a cure is effected, a lower dose appears to be safer or equally efficacious as a higher dose, or no continuing therapeutic effect is expected. In some embodiments, the methods can comprise increasing the administered amount of ubenimex if it is determined not to be efficacious, as well as stopping therapy if it is determined dose escalation or continued dosing at any dose is unlikely to be efficacious.

In some embodiments where the patient is undergoing treatment in accordance with the present disclosure, indications of NASH by abdominal imaging, ultrasound examination, magnetic resonance imaging, CT scan, and/or biopsy may be less than those measured in the patient prior to treatment, which is indicative that the patient is responding positively to the therapy. In cases where the patient is responding positively to a therapy of the present disclosure, the therapy is continued until the presence of the condition is reduced to a level comparable to a normal control level. Optionally, the therapy is continued to maintain alleviation of NASH symptoms. Alternatively, the therapy is continued until a desired level of steatosis is achieved in the patient (including the absence of steatosis). Treatment may be continued for so long as it is determined to be efficacious using assessment by abdominal imaging, ultrasound examination, magnetic resonance imaging, CT scan, and/or biopsy. The treatment may be determined to be efficacious through measured improvement in one or more of steatosis, ballooning, and necroinflammation. In one embodiment, the treatment is determined to be efficacious through measured improvement indicated by induced reduction in ballooning. In one embodiment, the treatment is determined to be efficacious through measured improvement indicated by a reduction in inflammation. In one embodiment, the treatment is determined to be efficacious through measured improvement indicated by at least one of reduced serum ALT levels, improved insulin sensitivity, reduced steatosis, reduced inflammation, reduced fibrosis, and increased PPAR (e.g., PPAR-alpha, PPAR-beta/delta, or PPAR-gamma) activation. In one embodiment, the treatment is determined to be efficacious through measured improvement indicated by induced regression or reversal of fibrosis and/or cirrhosis.

In some embodiments, treatment results in an improvement in one or more parameters (e.g., a reduction in NAS or SAF score, a reduction in hepatocyte ballooning, a reduction in fibrosis, or a reduction in CK-18 levels) of at least 10%, at least 20%, at least 30%, at least 40%, at least 50%, at least 60%, at least 70%, at least 80%, or at least 90% as compared to a control value. In some embodiments, treatment results in an improvement in one or more parameters of at least 2-fold, at least 3-fold, at least 4-fold, at least 5-fold, at least 6-fold, at least 7-fold, at least 8-fold, at least 9-fold, or at least 10-fold as compared to a control value. In some embodiments, the control value is a baseline value for the subject that is determined prior to the onset of treatment.

In some embodiments, the present disclosure provides methods of determining efficacy of a NASH treatment in a subject in need thereof by (a) measuring the level and severity of NASH via abdominal imaging, ultrasound examination, magnetic resonance imaging, CT scan, and/or liver biopsy in a subject in need thereof, where the level and severity of NASH is measured after treatment has started, (b) comparing the level and severity of NASH as measured in step (a) to a baseline level and severity of NASH, where the baseline level and severity is measured in the same subject before treatment is begun, and (c) determining the efficacy of the NASH treatment based on the comparison step.

Furthermore, in some embodiments the present disclosure provides methods of determining efficacy of a NASH treatment in a subject in need thereof by (a) measuring the level and severity of NASH in a subject in need thereof after treatment has begun, (b) comparing the level and severity of the NASH to a reference value, where the reference value represents an average value determined from a population of patients suffering from NASH, and (c) determining the efficacy of the NASH treatment based on the comparison step. In some embodiments, efficacy of therapy is determined by liver biopsy and analysis to evaluate NAFLD Activity Score (NAS) and fibrosis; the transjugular liver biopsy method can be employed for this purpose. Suitable patients include patients with biopsy proven NASH, patients at high risk for NASH, patients with a NAS greater than or equal to 4, NASH patients with liver fibrosis, and NASH patients with liver fibrosis of stage 2 or greater.

In some embodiments, patients responding to therapy in accordance with the invention are expected to show at least a slowing of any increase in CK-18 levels as therapy continues. In some embodiments, those patients responding most favorably to therapy will have CK-18 levels that stabilize and decline over time as full therapeutic benefit is realized. Thus, in some embodiments, the present disclosure provides methods of determining efficacy of a NASH treatment in a subject in need thereof by (a) measuring the level and severity of NASH via measuring the level of the biomarker CK-18 in a sample from the sample from the subject (e.g., a blood, plasma, or tissue sample), wherein the level and severity of NASH is measured after treatment has started, (b) comparing the level and severity of NASH measured in (a) to a baseline level and severity of NASH in the subject that is measured in the same subject before treatment is begun, and (c) determining the efficacy of the NASH treatment based on the comparison step; wherein a plateau or decrease in CK-18 levels is indicative of efficacy of the NASH treatment.

IV. Compositions, Unit Dosage Forms, and Kits Comprising Ubenimex

In another aspect, compositions, unit dosage forms, pharmaceutical packages, and kits comprising ubenimex for use in the methods described herein are provided. In some embodiments, the formulations, unit dosage forms, pharmaceutical packages, and/or kits are for use in treating NASH. In some embodiments, the formulations, unit dosage forms, pharmaceutical packages, and/or kits are for use in delaying or preventing the progression of NAFLD to NASH in a subject having NAFLD.

In some embodiments, the compositions, unit dosage forms, pharmaceutical packages, and/or kits comprise ubenimex or a pharmaceutically acceptable salt thereof. In some embodiments, the composition, unit dosage form, pharmaceutical package, or kit comprises ubenimex or ubenimex hydrochloride. In some embodiments, a composition or unit dosage form comprises ubenimex or a pharmaceutically acceptable salt thereof in an amount from about 10% to 50%, or from about 20% to about 40%, or about 30% to about 35%, or from about 15% to about 25% by weight of the total composition. In some embodiments, ubenimex is provided as an amorphous solid dispersion.

In some embodiments, ubenimex is formulated in a pharmaceutical composition comprising one or more pharmaceutically acceptable excipients. In some embodiments, an excipient comprises a solubilizing agent, a stabilizing agent, a diluent, an inert carrier, a preservative, a binder, a disintegrant, a coating agent, a flavoring agent, or a coloring agent. Suitable pharmaceutical compositions, formulations, and unit dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). Typically, pharmaceutical formulations of the disclosure comprise ubenimex and one or more pharmaceutically acceptable (approved by a state or federal regulatory agency for use in humans, or is listed in the U.S. Pharmacopia, the European Pharmacopia) excipients or carriers.

In some embodiments, at least one excipient is chosen to provide one or more beneficial physical properties to the formulation, such as increased stability and/or solubility of the active agent(s). Examples of suitable excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as TWEEN®, PLURONIC®, or polyethylene glycol (PEG); carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

In some embodiments, ubenimex is formulated as a liquid pharmaceutical composition, such as a composition comprising ubenimex in suspension, solution, or emulsion in an oily or aqueous vehicle. In some embodiments, the liquid composition further comprises one or more formulatory agents such as suspending, stabilizing, and/or dispersing agents. In some embodiments, solutions or suspensions used for the delivery of a drug in liquid formulation can include the following components: a sterile diluent such as water for injection, saline solution, fixed oils, polyethylene glycols, glycerine, propylene glycol, polysorbate, tocopherol polyethylene glycol succinate (TPGS), or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. These preparations can be enclosed in ampoules, disposable syringes or multiple dose vials made of glass or plastic.

In some embodiments, ubenimex is formulated for immediate release. As used herein, "immediate release" means a drug formulation that provides for the release of at least a majority of the drug within a relatively short period of time after administration (e.g., within about one hour). In some embodiments, an immediate release formulation provides for the release of at least about 80% of the drug within about 30-60 minutes after administration.

In some embodiments, ubenimex is formulated for sustained release or extended release. As used herein, "sustained release" and "extended release" means a drug formulation that provides for gradual release of a drug over an extended period of time, and typically, although not necessarily, results in substantially constant blood levels of a drug over an extended time period. In some embodiments, a sustained release formulation provides for a substantially constant blood level of the agent over a time period in the range of about 4 to about 12 hours, typically in the range of about 6 to about 10 hours. For example, a sustained release formulation can provide a very gradual increase in blood level of a drug following administration such that peak blood level is not reached until at least 4-6 hours have elapsed, with the rate of increase of blood level drug approximately linear, followed by a sustained period of peak blood levels and then by an equally gradual decrease in blood levels at the end of the sustained release period.

In some embodiments, ubenimex is formulated for delayed release. As used here, "delayed release" refers to a drug formulation that, following administration to a patient, provides a measurable time delay before drug is released from the formulation into the patient's body.

In some embodiments, oral ubenimex formulations are formulated as immediate release preparations, and are conveniently packaged, for example, in unit dosage forms in the form of a pill, capsule, or tablet, which in turn may be in a pill bottle or blister packaging, or, for liquid formulations of the drug, in liquid compatible containers. Dosages and desired drug concentration of pharmaceutical compositions of the disclosure may vary depending on the particular use envisioned. The determination of the appropriate dosage or route of administration is well within the skill of one in the art. Suitable dosages are also described in Section III above.

In some embodiments, ubenimex is provided in oral form in a fixed dosage amount in a unit dosage form that is a pill, tablet, or capsule containing amounts of ubenimex ranging from 5-1000 mg, 10-800 mg, 20-750 mg, 30-600 mg, 40-500 mg, 50-450 mg, 60-375 mg, 75-300 mg, 90-250 mg, or 100-150 mg. The particular unit dosage form will depend on the dose to be administered, which may depend on whether the patient is an adult or child or upon the severity of the disease.

In some embodiments, most adult patients (60-100 kg or more) will receive therapeutic benefit from a single dose in the range of 5-1000 mg per day, with some achieving full therapeutic effect with 5-450 mg at least once daily, 10-225 mg twice daily, or 5-150 mg three times daily. However, minimal doses of 10 mg, 30 mg, and 150 mg administered on these schedules (QD, BID, and TID) may be approved for clinical use. Some patients will administer the prescribed dose with each meal. Some patients will administer this dose before meals. Some patients will administer this dose as a chronic medication; it is anticipated that some patients will take the drug every day for periods of 6 months or longer.

The present disclosure also provides a variety of specific unit dosage forms suitable for use in the treatment methods described herein. For example, ubenimex can be administered in unit dosage forms containing from 5, 25, 30, 60, 90, or 150 mg of ubenimex, which are suitable for delivery one, twice, or three times a day to provide the daily dose prescribed by the physician in accordance with this disclosure. Moreover, previous formulations and unit dosage forms of ubenimex can be used in the methods of the disclosure. Ubenimex has been marketed for the treatment of cancer as an adjunct to chemotherapy agents to extent survival and maintain remission after treatment for acute non-lymphocytic leukemia under the brand name Bestatin™ in Japan and is being studied in the clinic for treatment of PAH (see, WO 2013/142369 and U.S. Pat. No. 9,233,089, each of which is incorporated herein by reference) and lymphedema (see, WO 2016/149126, incorporated herein by reference). In various embodiments of the disclosure, ubenimex, including but not limited to ubenimex in the Bestatin™ 10 mg or 30 mg unit dosage forms commercially available or in the forms being used in the PAH and lymphedema clinical trials, is administered to a patient with NASH.

In some embodiments, pharmaceutical packages and kits comprising ubenimex and a second therapeutic agent are provided. In some embodiments, the pharmaceutical package comprises ubenimex (e.g., in an immediate release, delayed release, or sustained release form) and a second therapeutic agent, wherein the second therapeutic agent is a farnesoid X receptor (FXR) agonist (including but not limiting to obeticholic acid); a peroxisome proliferator-activator receptor (PPAR) agonist, e.g., a PPAR-alpha agonist, a PPAR-beta/delta agonist, or a PPAR-gamma agonist (including but not limited to elafibranor); aramchol; a caspase inhibitor (including but not limited to emricasan); a galectin 3 inhibitor (including but not limited to GR-MD-02, Galectin Therapeutics); a MAPK5 inhibitor (including but not limited to GS-4997, Gilead Sciences); an FGF21 agonist (including but not limited to BMS-986036, Bristol-Myers Squibb); a LTD4 receptor antagonist (including but not limited to tipelukast); a niacin analog (including but not limited to ARI 3037MO, Arisaph Pharmaceuticals); an ASBT inhibitor (including but not limited to volixibat); an apoptosis signal regulating kinase 1 (ASK1) inhibitor; an angiotensin converting enzyme (ACE) inhibitor; an angiotensin receptor blocker (ARB, including but not limited to telmisartan); a chemokine receptor inhibitor (e.g., CCR2 and/or CCR5 inhibitors, including but not limited to cenicriviroc); a thiozolidinedione (including but not limited to rosiglitazone and pioglitazone); a GLP-1 analog (including but not limiting to semaglutide, liraglutide); a biguanide (e.g., metformin); or an NSAID. In some embodiments, the second therapeutic agent is not a chemotherapy agent.

In some embodiments, the pharmaceutical package or kit comprises unit dosage forms of ubenimex and further comprising unit dosage forms of a second therapeutic agent, wherein the second therapeutic agent is a FXR agonist, a PPAR agonist, aramchol, a caspase inhibitor, a galectin 3 inhibitor, a MAPK5 inhibitor, a FGF21 agonist, a LTD4 receptor antagonist, a niacin analog, an ASBT inhibitor, an ASK1 inhibitor, an ACE inhibitor, an angiotensin receptor blocker, a chemokine receptor inhibitor, a thiozolidinedione, a GLP-1 analog, a biguanide, or an NSAID.

In some embodiments, the pharmaceutical package or kit is for use in treating NASH. In some embodiments, the pharmaceutical package or kit is for use in delaying or preventing the progression of NAFLD to NASH in a subject having NAFLD. In some embodiments, the pharmaceutical package or kit further comprises instructional materials for use according to a method disclosed herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD-ROM), and the like. Such media may include addresses to internet sites that provide such instructional materials.

V. Combination Therapies for the Treatment of Nash

In another aspect, ubenimex is administered in combination with one or more additional therapeutic agents. In some embodiments, a method of treating NASH (and/or NAFLD) may further include in accordance with the disclosure a combination therapy in which a patient in need of treatment is administered ubenimex in combination with one or more drugs approved for the treatment of NASH (although there are none today, but such drugs includes drugs in clinical testing today that are later approved, if any), and/or an associated condition of NASH, or a combination thereof. Combination therapies for the treatment of NASH may further include administration of ubenimex in combination with one or more lifestyle changes, such as exercise to reduce body weight and/or activities to improve physical and/or mental health.

In some embodiments, ubenimex is administered in combination with one or more of a farnesoid X receptor (FXR) agonist (including but not limiting to obeticholic acid; EDP-305, Enanta Pharmaceuticals; and GS-9674, Gilead Sciences); a peroxisome proliferator-activator receptor (PPAR) agonist, e.g., a PPAR-alpha agonist, a PPAR-beta/delta agonist, and/or a PPAR-gamma agonist (including but not limited to elafibranor); aramchol; a caspase inhibitor (including but not limited to emricasan); a galectin 3 inhibitor (including but not limited to GR-MD-02, Galectin Therapeutics); a MAPK5 inhibitor (including but not limited to GS-4997, Gilead Sciences); an FGF19 agonist (including but not limited to NGM282, NGM Bio); an FGF21 agonist (including but not limited to BMS-986036, Bristol-Myers Squibb); a LTD4 receptor antagonist (including but not limited to tipelukast); a niacin analog (including but not limited to ARI 3037MO, Arisaph Pharmaceuticals); an ASBT inhibitor (including but not limited to volixibat); an apoptosis signal regulating kinase 1 (ASK1) inhibitor; a chemokine receptor inhibitor (e.g. CCR2 and/or CCR5 inhibitors, including but not limited to cenicriviroc); a thiozolidinedione (including but not limited to rosiglitazone and pioglitazone); a GLP-1 analog (including but not limiting to semaglutide, liraglutide); a biguanide (e.g. metformin); a nonsteroidal anti-inflammatory drug ("NSAID") (e.g., aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, and tiaprofenic acid); an antidiabetic (e.g., biguanides, sulfonylureas, meglitinides, thiazolidinediones, tiazolidinediones, pioglitazone, dipeptidyl peptidase IV inhibitors, and a-glucosidase inhibitors); a lipid-lowering agent (e.g., atorvastatin, rosuvastatin, fluvastatin, lovastatin, simvastatin, pravastatin, pitavastatin, niacin, fenofibrate, fenofibric acid, gemfibrozil, and omega-3 polyunsaturated fatty acid), an angiotensin converting enzyme (ACE) inhibitor (e.g., captopril, enalapril, lisinopril, benazepril, fosinopril, quinapril, and ramipril); an angiotensin II receptor blocker ("ARBs") (e.g., irbesartan, losartan, olmesartan, valsartan, and telmisartan), anti-angiogenic agents (e.g., sorafenib); vitamin E; an antiplatelet agent (e.g., aspirin); an anti-obesity or appetite suppressant (e.g., phentermine, orlistat, lorcaserin, phendimetrazine, methamphetamine, benzphatamine, diethylpropion, sibutramine, topiramate, and bupropion); an psychosomatic agent (e.g., antidepressants, and antipsychotics), a Acetyl-CoA carboxylase inhibitor (including but not limited to GS-0976, Gilead); a PDE-5 inhibitor; or a deacetylase sirtuin stimulator. In some embodiments, ubenimex is not administered in combination with a chemotherapy agent.

In one embodiment, the present disclosure comprises a combination therapy wherein ubenimex is administered in combination with an ACE inhibitor. In one embodiment, ubenimex is administered in combination with telmisartan. In one embodiment, ubenimex is administered in combination with one or more CCR2/CCR5 inhibitors. In one embodiment, ubenimex is administered in combination with cenicriviroc. In one embodiment, ubenimex is administered in combination with a thiazolidinedione, for example, rosiglitazone or pioglitazone. In one embodiment, ubenimex is administered in combination with metformin. In one embodiment, ubenimex is administered in combination with an FXR agonist, including but not limited to Ocaliva (obeticholic acid), which is approved for biliary cholangitis. In one embodiment, ubenimex is administered in combination with a PPAR alpha/delta agonist, including but not limited to Elafibranor, currently in clinical trials. In some embodiments, ubenimex is administered in combination with a compound disclosed in Musso et al., *Nature Reviews Drug Discovery*, 2016, 15:249-274.

In some embodiments, ubenimex is administered in combination with telmisartan or losartan. In some embodiments, ubenimex is administered a dosage of about 10 mg to about 450 mg and telmisartan is administered at a dosage of about 20 to 80 mg (e.g., QD or BID).

In some embodiments, ubenimex is administered in combination with obeticholic acid (OCA). In some embodiments, ubenimex is administered a dosage of about 10 mg to about 450 mg and OCA is administered at a dosage of 10, 25, or 40 mg (e.g., QD or BID).

In some embodiments, ubenimex is administered in combination with volixibat. In some embodiments, ubenimex is administered a dosage of about 10 mg to about 450 mg and volixibat is administered at a dosage of about 5 to 20 mg (e.g., QD or BID).

In some embodiments, ubenimex is administered in combination with aramchol. In some embodiments, ubenimex is administered a dosage of about 10 mg to about 450 mg and aramchol is administered at a dosage of about 100 to 300 mg (e.g., QD or BID).

In some embodiments, ubenimex is administered in combination with elafibranor. In some embodiments, ubenimex is administered a dosage of about 10 mg to about 450 mg and elafibranor is administered at a dosage of about 120 mg (e.g., QD or BID).

The beneficial effect of the combination or ubenimex and a second therapeutic agent may include, but is not limited to, pharmacokinetic or pharmacodynamic co-action resulting from the combination of therapeutic agents. Such combination therapies can result in an improved parameter such as, but not limited to, improved NASH scores (e.g., as measured by the NAFLD Activity Score), decreased fibrosis scores, and decreased serum alanine aminotransferase (ALT) levels; improved insulin sensitivity in adipose tissue (including but not limited to by activating PPAR gamma); biochemical and histological improvements in NASH; improved (decreased) insulin resistance; and improvements in steatosis, inflammation, and fibrosis.

Administration of therapeutic agents in combination typically is carried out over a defined time period (e.g., over a period of days, weeks, or months depending upon the combination selected). Combination therapy includes administration of at least two different therapeutic agents in a sequential manner, wherein each therapeutic agent is administered at a different time, as well as administration of at least two different therapeutic agents in a substantially simultaneous manner. Substantially simultaneous administration can be accomplished, for example, by administering to the subject a single capsule having a fixed ratio of each therapeutic agent or in separate capsules for each of the therapeutic agents. In some embodiments, the ubenimex and the second therapeutic agent are formulated separately. In some embodiments, the ubenimex and the second therapeutic agent are formulated in a single composition.

Sequential or substantially simultaneous administration of each therapeutic agent can be effected by any appropriate route, including, but not limited to, oral routes, intravenous routes, intramuscular routes, and direct absorption through mucous membrane tissues. The two different therapeutic agents can be administered by the same route or by different routes. For example, a first therapeutic agent of the combination selected may be administered by intravenous injection while the second therapeutic agent of the combination may be administered orally. Alternatively, for example, all therapeutic agents may be administered orally or all therapeutic agents may be administered by intravenous injection.

For the combination therapies disclosed herein, it is contemplated that each agent can be administered in an "immediate release" manner or in a "controlled release" or "delayed release" manner. When the additional active agent is an anti-inflammatory, for instance, any dosage form containing both active agents, i.e., both the ubenimex and the anti-inflammatory, can provide for immediate release or controlled release of the anti-inflammatory, and either immediate release or controlled release of the ubenimex.

As a non-limiting example, a combination dosage form for once-daily administration may contain in the range of about 5 mg to about 450 mg of ubenimex in a controlled release (e.g., sustained or extended release) or immediate release form, and a secondary agent in immediate release form, or in controlled release form, with the additional active agent present in an amount that provides a weight ratio of the ubenimex to the secondary agent. In other formulations, two or more secondary agents, which may or may not be in the same class of drug (e.g., anti-inflammatories), can be present in combination, along with ubenimex. In such a case, the effective amount of either or each individual secondary agents present will generally be reduced relative to the amount that would be required if only a single added agent were used.

Combination therapy also includes the administration of the different therapeutic agents as described above in further combination with other biologically active ingredients and non-drug therapies (e.g., surgery or physical therapy). Where a combination therapy comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

EXAMPLES

The following examples are offered to illustrate, but not to limit, the claimed invention.

Example 1: Anti-NASH Efficacy of Ubenimex in an Animal Model

The STAM™ mouse is a model for NASH created by a combination of chemical and dietary interventions in C57BL/6 mice that manifest NASH at about 8 weeks, which progresses to fibrosis at about 12 weeks and then progresses to HCC at about 16 weeks. See, Saito et al., *Sci. Rep.* 2015, 5:12466. This model was used in the study described herein to demonstrate the efficacy of ubenimex in treating NASH.

In the study, the control groups were as follows: (i) Untreated Disease Control—a group of STAM mice injected with streptozotocin (STZ, Sigma-Aldrich, USA) at 2 days old, and fed a high fat diet (HFD, 57 kcal % fat, Cat #HFD32, CLEA Japan, Japan) starting at 4 weeks old; and (ii) Positive Control—a group of STAM mice treated with telmisartan (10 mg/kg QD from 7 to 9 weeks). In addition to these control groups, test groups of STAM mice treated with a low dose of ubenimex (5 mg/kg ubenimex BID from 7 to 9 weeks) or a high dose of ubenimex (25 mg/kg BID from 7 to 9 weeks), were included in the study. The low dose is equivalent to a human dose of 30 mg BID. The high dose is equivalent to a human dose of 150 mg BID. The viability, clinical signs and behavior were monitored daily, including body weight, signs of toxicity, moribundity and mortality. The mice were maintained in a SPF facility under controlled conditions of temperature (23±2° C.), humidity (45±10%), lighting (12-hour artificial light and dark cycles; light from 8:00 to 20:00) and air exchange. A high pressure was maintained in the experimental room to prevent contamination of the facility. The mice were housed in TPX cages (CLEA Japan) with a maximum of 4 mice per case.

All groups of mice were sacrificed at 9 weeks. Once sacrificed, the body weight of each mouse was recorded. The liver of each mouse was removed and weighed. The liver-to-body weight ratio was determined for each mouse. Blood serum levels of CK-18, ALT, and liver triglycerides were determined for each mouse. The livers were then sectioned and stained with hematoxylin and eosin ("HE") stain, as well as Sirius red staining, to determine liver steatosis (ballooning) and fibrosis, respectively.

Table 1 below shows the results of the body and liver weight testing, which generally indicated that the ubenimex treatment was safe. Generally, the telmisartan group showed a significant decrease in mean body weight on the day of sacrifice compared with the control group. The low and high dose groups tended to decrease in mean body weight on the day of sacrifice, as compared with the control group. The high dose, low dose, and telmisartan groups showed significant decreases in mean liver weight compared with the control group. The high dose and telmisartan groups tended to decrease mean liver-to-body weight ratio as compared with the control group. There was no significant difference in mean liver-to-body weight ratio between the control group and the low dose group.

TABLE 1

Body weight and liver weight

| Parameter (mean ± SD) | Disease-control (n = 8) | Ubenimex, 5 mg/kg BID (n = 6) | Ubenimex, 25 mg/kg BID (n = 7) | Telmisartan, 10 mg/kg QD (n = 8) |
|---|---|---|---|---|
| Body weight (g) | 18.8 ± 1.6 | 16.6 ± 2.8 | 17.7 ± 1.1 | 15.8 ± 2.0 |
| Liver weight (mg) | 1420 ± 165 | 1206 ± 143 | 1190 ± 83 | 1027 ± 76 |
| Liver-to-body weight ratio (%) | 7.6 ± 1.1 | 7.4 ± 1.2 | 6.7 ± 0.3 | 6.6 ± 0.6 |

Table 2 below shows that the high and low dose ubenimex groups and the positive control telmisartan group all showed significant reductions in NAFLD activity score (NAS) as compared with the control group.

TABLE 2

NAFLD Activity Score

| Group | n | Steatosis 0 | 1 | 2 | 3 | Lobular inflammation 0 | 1 | 2 | 3 | Hepatocyte ballooning 0 | 1 | 2 | NAS (mean ± SD) |
|---|---|---|---|---|---|---|---|---|---|---|---|---|---|
| Disease-control | 8 | — | 7 | 1 | — | — | — | 6 | 2 | — | 2 | 6 | 5.1 ± 1.0 |
| Ubenimex, 5 mg/kg BID | 6 | 1 | 5 | — | — | — | 1 | 3 | 2 | 4 | 2 | — | 3.3 ± 0.5 |
| Ubenimex, 25 mg/kg BID | 7 | — | 7 | — | — | — | — | 5 | 2 | 5 | 2 | — | 3.6 ± 0.5 |
| Telmisartan, 10 mg/kg QD | 8 | 3 | 5 | — | — | — | 2 | 4 | 2 | 8 | — | — | 2.6 + 0.9 |

Definitions of NAS Components

| Item | Score | Extent |
|---|---|---|
| Steatosis | 0 | <5% |
|  | 1 | 5-33% |
|  | 2 | >33-66% |
|  | 3 | >66% |
| Lobular inflammation | 0 | No foci |
|  | 1 | <2 foci/200x |
|  | 2 | 2-4 foci/200x |
|  | 3 | >4 foci/200x |
| Hepatocyte ballooning | 0 | None |
|  | 1 | Few balloon cells |
|  | 2 | Many cells/prominent ballooning |

As shown in Table 2, ubenimex therapy demonstrated significant reduction in NAS as compared to the negative control group. NAS is one of the clinical endpoints for assessing the activity of NASH (Sanyal et al., *Hepatology*, 2011, 54:344), and thus is the key preclinical endpoint in clinical translation. The improvement of NAS by ubenimex was, at this time point, attributable to the changes in hepatocyte ballooning, which was significantly decreased compared with the control group. Rangwala reported the close association of hepatocyte ballooning and NASH-related fibrosis (Rangwala et al., *J. Pathol*, 2011, 224:401), which indicates that continued treatment should have a positive impact on fibrosis. Consistent with this, treatment with ubenimex was observed in the low dose (e.g., 5 mg/kg BID) group to tend to reduce the pathological deposition of collagen in the liver, as demonstrated by Sirius red staining. Thus, reduction of hepatocyte ballooning in the high and low dose ubenimex groups is indicative not only of a positive treatment impact but strong support for continuing therapy to increase the anti-fibrosis effects of this treatment.

As shown in Table 3 below, no significant effect on plasma ALT or liver triglyceride levels were seen in the test groups, although the telmisartan positive control group reflected a trend of decreased levels of both relative to the disease (negative) control group. It is believed that continued administration of ubenimex would reduce these levels.

Plasma CK-18 (in units of mIU/mL) was measured and found to be significantly lower in the low and high dose ubenimex groups (238.5±7.7 and 230.8±28.6, respectively) and relatively unchanged between the control and telmisartan groups (292.3±28.5 and 284.5±38.4, respectively). These results convincingly demonstrate that ubenimex has a different and potentially more potent therapeutic benefit than telmisartan.

Plasma LTB4 levels were measured but were not considered meaningful in that while the ubenimex low dose and telmisartan groups showed some tendency to increase plasma LTB4 relative to the control, the control and ubenimex high dose levels measured were not statistically different, and there was significant variability in all but the control group.

These results support continued studies of ubenimex in NASH animal models and human clinical trials.

Example 2: Ubenimex Human Clinical Trials

Two or more groups of human subjects affected by NASH are each administered a pharmaceutically effective dose of ubenimex comprising 30 mg, with one group receiving QD administration (i.e., a total daily dose of 30 mg) and the other BID (i.e., a total daily dose of 60 mg). A human control group affected by NASH is administered a placebo. The

TABLE 3

Biochemistry

| Parameter (mean ± SD) | Disease-control (n = 8) | Ubenimex, 5 mg/kg BID (n = 6) | Ubenimex, 25 mg/kg BID (n = 7) | Telmisartan, 10 mg/kg QD (n = 8) |
| --- | --- | --- | --- | --- |
| Plasma ALT (U/L) | 59 ± 27 | 59 ± 22 | 62 ± 11 | 44 ± 13 |
| Liver triglyercide (mg/g liver) | 46.4 ± 16.5 | 50.0 ± 22.7 | 34.8 ± 22.2 | 22.4 ± 7.5 |

As shown in Table 4, liver sections from the disease control group showed increased collagen deposition in the pericentral region of liver lobule. The telmisartan group showed a significant decrease in the fibrosis area (Sirius red-positive area) as compared with the control group. The low dose group showed a tendency to decrease the fibrosis area compared to the disease control group, but this was not seen in the high dose group (no significant difference in fibrosis area between the control group and the high dose group). In this proof-of-concept study designed to evaluate efficacy of ubenimex on NASH only, the animals were sacrificed at age of 9 weeks while full development of liver fibrosis in this animal model typically occurs at age of 12 weeks. it is believed that longer duration of treatment in animals allowed for full development of fibrosis would have resulted in a more profound therapeutic effect in both treatment dose groups.

study is conducted for approximately 6 months, during which the participants are monitored for improvements in at least one of NAFLD Activity Score, Steatosis Score, Inflammation Score, and Ballooning Score. Treatment is anticipated to improve one or more of said scores.

Example 3: In Vivo Efficacy Study of Ubenimex in STAM Model of NASH with Fibrosis This study examined the effects of ubenimex in a STAM model of NASH fibrosis at multiple dosing regimens.

Materials and Methods

NASH was induced in 40 male mice by a single subcutaneous injection of 200 μg streptozotocin (STZ, Sigma-Aldrich, USA) solution 2 days after birth and feeding with a high fat diet (HFD, 57 kcal % fat, Cat #HFD32, CLEA Japan Inc., Japan) after 4 weeks of age.

TABLE 4

Fibrosis Area

| Parameter (mean ± SD) | Disease-control (n = 8) | Ubenimex, 5 mg/kg BID (n = 6) | Ubenimex, 25 mg/kg BID (n = 7) | Telmisartan, 10 mg/kg QD (n = 8) |
| --- | --- | --- | --- | --- |
| Sirius red-positive area (%) | 1.02 ± 0.32 | 0.80 ± 0.16 | 1.05 ± 0.14 | 0.71 ± 0.15 |

Ubenimex or telmisartan was administered orally in a volume at 10 mL/kg. Ubenimex was administered at a dose of 5 mg/kg once daily or twice daily. Telmisartan was administered at a dose of 5 mg/kg once daily.

C57Bl/6 mice (14-day-pregnant females) were obtained from Japan SLC, Inc. (Japan). All animals used in the study were housed and cared for in accordance with the Japanese Pharmacological Society Guidelines for Animal Use. The animals were maintained in a SPF facility under controlled conditions of temperature (23±2° C.), humidity (45±10%), lighting (12-hour artificial light and dark cycles; light from 8:00 to 20:00) and air exchange. A high pressure was maintained in the experimental room to prevent contamination of the facility. The mice were housed in TPX cages (CLEA Japan) with a maximum of 4 mice per case. Sterilized solid HFD and pure water were provided ad libitum.

Measurement of Plasma Biochemistry:

For plasma biochemistry, blood was collected in polypropylene tubes with anticoagulant (Novo-Heparin, Mochida Pharmaceutical Co. Ltd., Japan) and centrifuged at 1,000×g for 15 minutes at 4° C. The supernatant was collected and stored at −80° C. until use. Plasma ALT level was measured by FUJI DRI-CHEM 7000 (Fujifilm, Japan).

Measurement of Liver Triglyceride Content:

Liver total lipid-extracts were obtained by Folch's method (Folch et al., J. Biol Chem, 1957, 226:497). Liver samples were homogenized in chloroform-methanol (2:1 v/v) and incubated overnight at room temperature. After washing with chloroform-methanol-water (8:4:3 v/v/v), the extracts were evaporated to dryness and dissolved in isopropanol. Liver triglyceride content was measured by Triglyceride E-test (Wako Pure Chemical Industries, Ltd., Japan).

Histological Analyses:

For HE staining, sections were cut from paraffin blocks of liver tissue prefixed in Bouin's solution and stained with Lillie-Mayer's hematoxylin (Muto Pure Chemicals Co., Ltd., Japan) and eosin solution (Wako Pure Chemical Industries, Ltd., Japan). NAFLD Activity Score (NAS) was calculated according to the criteria of Kleiner (Kleiner et al., *Hepatology*, 2005, 41:1313). To visualize collagen deposition, Bouin's fixed liver sections were stained using picro-Sirius red solution (Waldeck, Germany). For quantitative analysis of fibrosis area, bright field images of Sirius red-staining sections were captured around the central vein using a digital camera (DFC295; Leica, Germany) at 200-fold magnification, and the positive areas in 5 fields/section were measured using ImageJ software (National Institutes of Health, USA).

Statistical tests: Statistical analyses were performed using Bonferroni Multiple Comparison Test on GraphPad Prism 6 (GraphPad Software Inc., USA). P values <0.05 were considered statistically significant. A trend or tendency was assumed when a one-tailed t-test returned P values <0.1. Results were expressed as mean±SD.

Experimental Design and Treatment

Study groups: The following study groups were used. Group 1 (Vehicle): 8 NASH mice were orally administered vehicle (RO water) in a volume of 10 mL/kg twice daily from 6 to 11 weeks of age. Group 2 (Ubenimex QD for 5 weeks): 8 NASH mice were orally administered vehicle supplemented with ubenimex at a dose of 5 mg/kg once daily from 6 to 11 weeks of age. Group 3 (Ubenimex BID for 5 weeks): 8 NASH mice were orally administered vehicle supplemented with ubenimex at a dose of 5 mg/kg twice daily from 6 to 11 weeks of age. Group 4 (Ubenimex BID for 2 weeks): 8 NASH mice were orally administered vehicle supplemented with ubenimex at a dose of 5 mg/kg twice daily from 9 to 11 weeks of age. Group 5 (Telmisartan for 5 weeks): 8 NASH mice were orally administered pure water supplemented with telmisartan at a dose of 5 mg/kg once daily from 6 to 11 weeks of age.

Animal monitoring and sacrifice: The viability, clinical signs, and behavior were monitored daily. Body weight was recorded before the treatment. Mice were observed for significant clinical signs of toxicity, moribundity and mortality approximately 60 minutes after each administration. The animals were sacrificed by exsanguination through direct cardiac puncture under isoflurane anesthesia.

Results

Mean body weight of the day of sacrifice, mean liver weight, and mean liver-to-body weight ratio are shown in Table 5 below for all five groups. The mean body weight on the day of sacrifice was significantly decreased in the ubenimex BID for 5 weeks group and telmisartan positive control group as compared with the vehicle group. The mean body weight on the day of sacrifice tended to decrease in the ubenimex QD group as compared with the vehicle group. There were no significant differences in mean body weight on the day of sacrifice between the vehicle group and the ubenimex BID for 2 weeks group. For liver weight, the telmisartan group showed a significant decrease in mean liver weight as compared with the vehicle group. Mean liver weight tended to decrease in the ubenimex QD and ubenimex BID for 5 weeks groups as compared with the vehicle group. There were no significant differences in mean liver weight between the vehicle group and the ubenimex BID for 2 weeks group. The telmisartan group showed a significant decrease in mean liver-to-body weight ratio as compared with the vehicle group. There were no significant differences in mean liver-to-body weight ratio between the vehicle group and the ubenimex treatment groups.

TABLE 5

Body weight and liver weight

| Parameter (mean ± SD) | Group 1 (vehicle) (n = 6) | Group 2 (UBX QD; 5 weeks) (n = 6) | Group 3 (UBX BID; 5 weeks) (n = 6) | Group 4 (UBX BID; 2 weeks) (n = 6) | Group 5 (Telmisartan; 5 weeks) (n = 6) |
|---|---|---|---|---|---|
| Body weight (g) | 22.3 ± 3.1 | 19.9 ± 1.5 | 18.7 ± 1.6 | 21.3 ± 2.2 | 18.3 ± 1.9 |
| Liver weight (mg) | 1806 ± 263 | 1526 ± 191 | 1539 ± 258 | 1603 ± 321 | 1105 ± 105 |
| Liver-to-body weight ratio (%) | 8.1 ± 1.1 | 7.7 ± 0.9 | 8.3 ± 1.2 | 7.5 ± 0.9 | 6.1 ± 0.5 |

As shown in Table 6 below, plasma ALT level tended to decrease in the telmisartan group as compared to the vehicle group, although this difference was not statistically significant. There were no significant differences in plasma ALT levels between the vehicle group and the ubenimex treatment groups.

Liver triglyceride content tended to decrease in the telmisartan group as compared to the vehicle group (Table 6), although this difference was not statistically significant. There were no significant differences in liver triglyceride content between the vehicle group and the ubenimex treatment groups.

TABLE 6

| | Biochemistry | | | | |
|---|---|---|---|---|---|
| Parameter (mean ± SD) | Group 1 (vehicle) (n = 6) | Group 2 (UBX QD; 5 weeks) (n = 6) | Group 3 (UBX BID; 5 weeks) (n = 6) | Group 4 (UBX BID; 2 weeks) (n = 6) | Group 5 (Telmisartan; 5 weeks) (n = 6) |
| Plasma ALT (U/L) | 56 ± 33 | 85 ± 64 | 52 ± 21 | 47 ± 24 | 36 ± 11 |
| Liver triglyceride (mg/g liver) | 60.4 ± 22.6 | 58.6 ± 24.4 | 59.6 ± 21.4 | 62.0 ± 33.5 | 24.6 ± 8.4 |

Figure 1B:
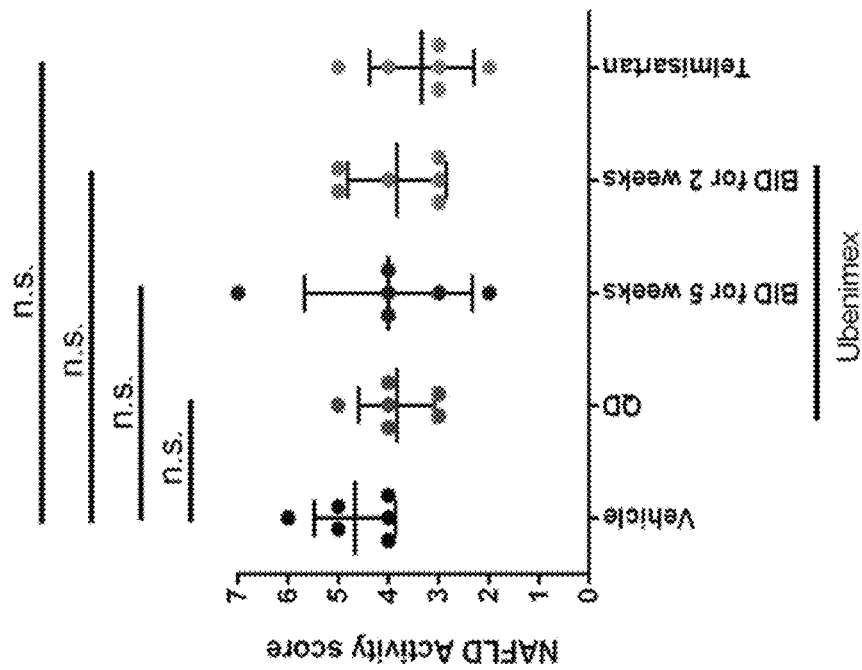
Figure 1D:
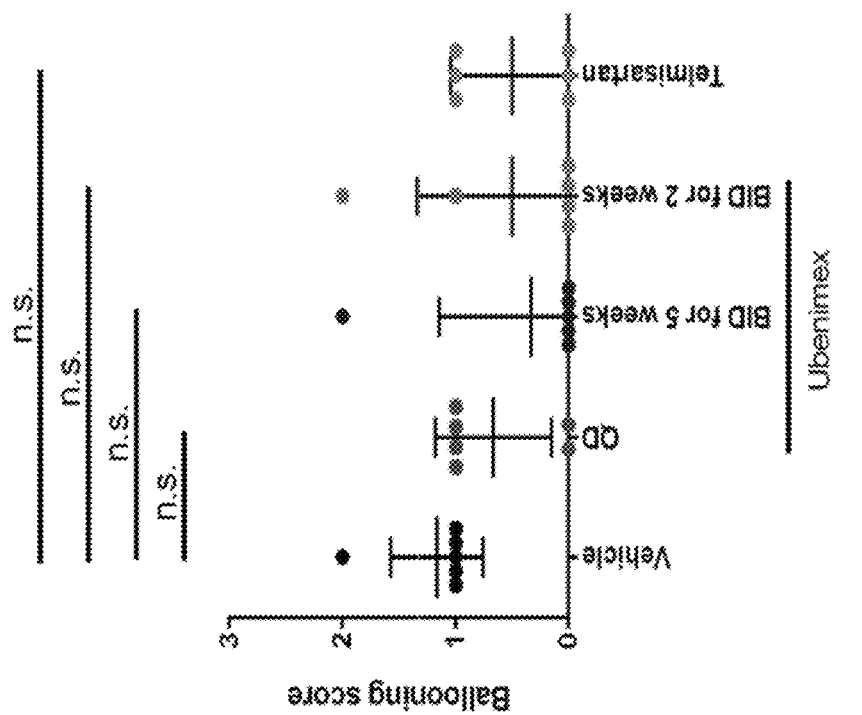
Figure 1C:
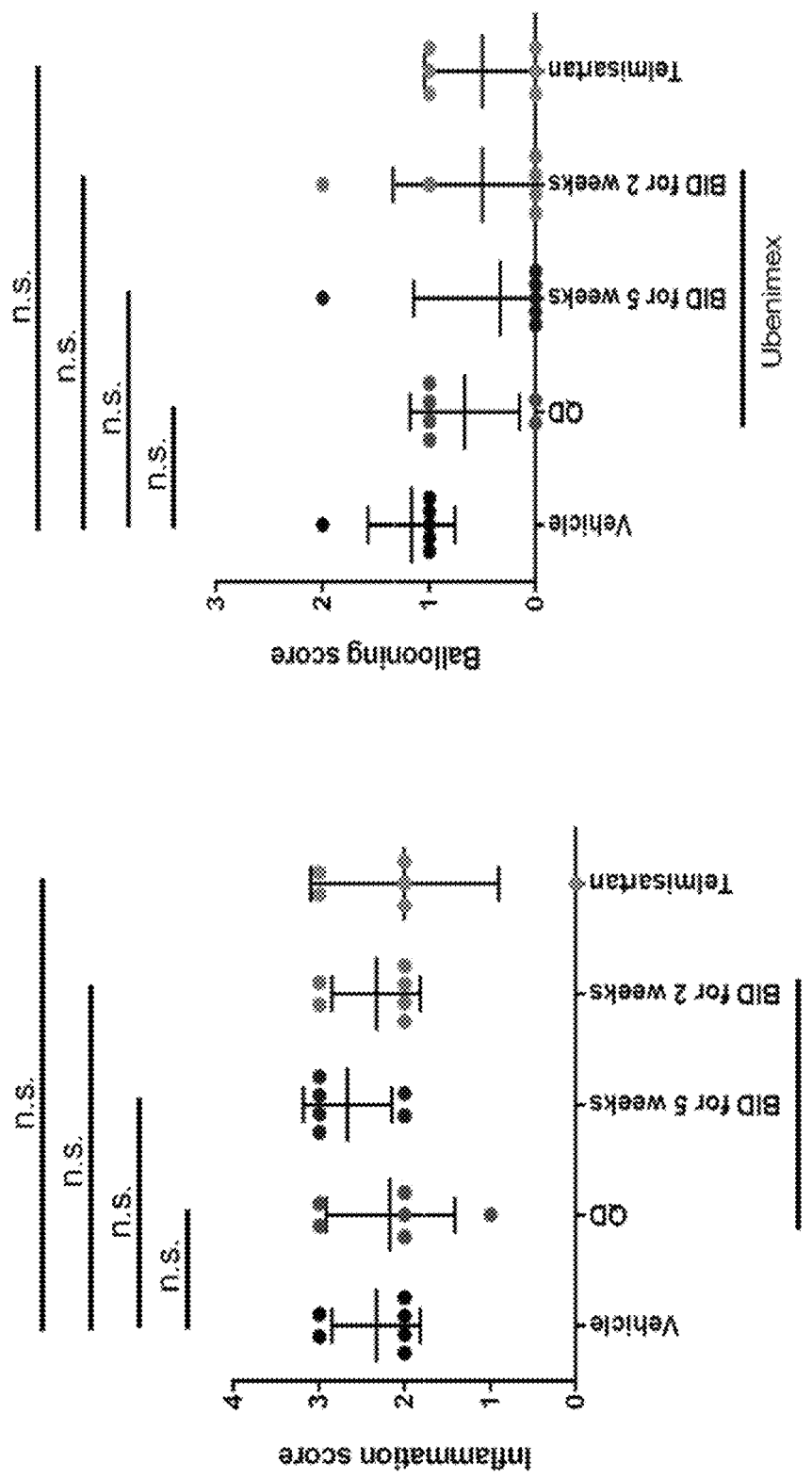

FIG. 1A and Table 7 show that NAFLD activity score (NAS) tended to decrease in the ubenimex treatment groups and positive control telmisartan group as compared with the control group. The NAFLD activity score is determined from a combination of steatosis score, inflammation score, and hepatocyte ballooning score. As shown in FIGS. 1B-D and Table 7, although no significant differences were observed between the vehicle group and the ubenimex therapy or telmisartan groups with respect to the steatosis score or inflammation score, hepatocyte ballooning tended to decrease in the ubenimex treatment groups and positive control telmisartan group as compared to the vehicle group. Using the student t-test, a significant decrease was observed for hepatocyte ballooning score between the group treated with ubenimex BID for 5 weeks and the control group ($p=0.0493$). As discussed in Example 1 above, Rangwala reported the close association of hepatocyte ballooning and NASH-related fibrosis, which indicates that continued treatment should have a positive impact on fibrosis. Consistent with this hypothesis, treatment with QD ubenimex for 5 weeks was observed to tend to decrease the fibrosis area, as demonstrated by Sirius red staining (see Table 8 below). The reduction of hepatocyte ballooning in the ubenimex treatment groups is indicative of a positive therapeutic effect by ubenimex in the treatment of NASH.

TABLE 7

| | | NAFLD Activity Score | | | | | | | | | | |
|---|---|---|---|---|---|---|---|---|---|---|---|---|
| | | Score | | | | | | | | | | |
| | | Steatosis | | | | Lobular inflammation | | | | Hepatocyte ballooning | | | NAS |
| Group | n | 0 | 1 | 2 | 3 | 0 | 1 | 2 | 3 | 0 | 1 | 2 | (mean ± SD) |
| Vehicle | 6 | — | 5 | 1 | — | — | — | 4 | 2 | — | 5 | 1 | 4.7 ± 0.8 |
| UBX QD; 5 weeks | 6 | — | 6 | — | — | — | 1 | 3 | 2 | 2 | 4 | — | 3.8 ± 0.8 |
| UBX BID; 5 weeks | 6 | 1 | 4 | 1 | — | — | — | 2 | 4 | 5 | — | 1 | 4.0 ± 1.7 |
| UBX BID; 2 weeks | 6 | 1 | 4 | 1 | — | — | — | 4 | 2 | 4 | 1 | 1 | 3.8 ± 1.0 |
| Telmisartan; 5 weeks | 6 | 1 | 5 | — | — | 1 | — | 3 | 2 | 3 | 3 | — | 3.3 ± 1.0 |

Definitions of NAS components are shown in Table 2 above.

Liver sections from the vehicle control group showed increased collagen deposition in the pericentral region of liver lobule. As shown in Table 8 below, the telmisartan positive group showed a significant decrease in the fibrosis area (Sirius red-positive area) as compared with the vehicle group. The fibrosis area tended to decrease in the ubenimex QD group as compared with the vehicle group.

TABLE 8

Fibrosis area.

| Parameter (mean ± SD) | Group 1 (vehicle) (n = 6) | Group 2 (UBX QD; 5 weeks) (n = 6) | Group 3 (UBX BID; 5 weeks) (n = 6) | Group 4 (UBX BID; 2 weeks) (n = 6) | Group 5 (Telmisartan; 5 weeks) (n = 6) |
|---|---|---|---|---|---|
| Sirius red-positive area (%) | 1.03 ± 0.45 | 0.75 ± 0.16 | 0.88 ± 0.22 | 0.87 ± 0.14 | 0.57 ± 0.14 |

In summary, treatment with ubenimex once daily for a longer period of time (5 weeks) showed decreasing trends in NAS scores and fibrosis, as shown by the data in FIGS. 1A and 1n Tables 7 and 8. Treatment with ubenimex twice daily for a shorter period of time (2 weeks) showed decreasing trends in NAS scores, as shown by the data in FIGS. 1A and 1n Table 7. As shown in FIG. 1D and Table 7, the improvement in NAS scores was characterized by a reduction in the hepatocyte ballooning score.

While this disclosure has been particularly shown and described with references to preferred embodiments thereof, it will be understood by those skilled in the art that various changes in form and details may be made therein without departing from the scope of the disclosure encompassed by the appended claims.

All publications, patents, patent applications, or other documents cited herein are hereby incorporated by reference in their entirety for all purposes to the same extent as if each individual publication, patent, patent application, or other document was individually indicated to be incorporated by reference for all purposes.

What is claimed is:

1. A method of treating NASH or slowing the progression of NAFLD to NASH, the method comprising administering a therapeutically effective dose of ubenimex and a therapeutically effective dose of a second therapeutic agent to a subject in need thereof, wherein the second therapeutic agent is a FXR agonist, a PPAR agonist, aramchol, a caspase inhibitor, a galectin 3 inhibitor, a MAPK5 inhibitor, a FGF19 agonist, a FGF21 agonist, a LTD4 receptor antagonist, a niacin analog, an ASBT inhibitor, an ASK1 inhibitor, an ACE inhibitor, an angiotensin receptor blocker, a chemokine receptor inhibitor, a thiozolidinedione, a GLP-1 analog, a biguanide, or an NSAID, wherein the ubenimex is administered for at least 4 weeks.

2. The method of claim 1, wherein the ubenimex is administered for at least 12 weeks.

3. The method of claim 2, wherein the ubenimex is administered for at least 24 weeks.

4. A method of treating non-alcoholic steatohepatitis (NASH), the method comprising administering to a subject in need of treatment a therapeutically effective amount of ubenimex, wherein the ubenimex is administered at a daily dose of about 20 mg to about 450 mg QD.

5. The method of claim 4, wherein the ubenimex is administered orally, intranasally, rectally, topically, intraperitoneally, intravenously, intramuscularly, subcutaneously, subdermally, transdermally, or intrathecally.

6. A method of treating non-alcoholic steatohepatitis (NASH), the method comprising administering to a subject in need of treatment a therapeutically effective amount of ubenimex, wherein the ubenimex is administered at a daily dose of about 10 mg to about 200 mg BID.

7. The method of claim 6, wherein the ubenimex is administered at a dose of about 10 mg to about 150 mg TID.

8. The method of claim 6, wherein the ubenimex is administered orally, intranasally, rectally, topically, intraperitoneally, intravenously, intramuscularly, subcutaneously, subdermally, transdermally, or intrathecally.

9. The method of claim 4 or 6, wherein the ubenimex is administered once daily, twice daily, or three times daily.

10. A method of treating non-alcoholic steatohepatitis (NASH), the method comprising administering to a subject in need of treatment a therapeutically effective amount of ubenimex, wherein the ubenimex is administered until a therapeutic improvement is observed for the subject, and wherein the therapeutic improvement comprises a reduction of at least 10% in at least one of fibrosis, hepatocyte ballooning, inflammation, steatosis, or lobular inflammation in the subject.

11. The method of claim 10, wherein the therapeutic improvement is measured using at least one of a non-alcoholic fatty liver disease (NAFLD) activity score, a fatty liver index, a hepatic steatosis index, a NAFLD liver fat score, a steatosis, activity, and fibrosis (SAF) score, a NAFLD fibrosis score, or a serum biomarker.

12. The method of claim 11, wherein the serum biomarker comprises at least one of plasma CK-18, alanine aminotransferase (ALT), or liver triglycerides.

13. The method of claim 10, wherein the therapeutic improvement comprises a reduction in hepatocyte ballooning in the subject.

14. The method of claim 10, wherein the ubenimex is administered in combination with a second therapeutic agent.

15. The method of claim 14, wherein the second therapeutic agent is a farnesoid X receptor (FXR) agonist, a peroxisome proliferator-activator receptor (PPAR) agonist, aramchol, a caspase inhibitor, a galectin 3 inhibitor, a mitogen-activated protein kinase 5 (MAPK5) inhibitor, a fibroblast growth factor 19 (FGF19) agonist, a FGF21 agonist, a leukotriene D4 (LTD4) receptor antagonist, a niacin analog, an apical sodium bile acid cotransporter (ASBT) inhibitor, an apoptosis signal regulating kinase 1 (ASK1) inhibitor, an angiotensin converting enzyme (ACE) inhibitor, an angiotensin receptor blocker, a chemokine receptor inhibitor, a thiozolidinedione, a GLP-1 analog, a biguanide, or a non-steroidal anti-inflammatory drug (NSAID).

16. The method of claim 14, wherein the method results in an improvement in at least one of insulin sensitivity, insulin resistance, steatosis, inflammation, or fibrosis.

17. The method of claim 10, wherein the ubenimex is administered at a dose of about 5 mg to about 450 mg.

18. The method of claim 10, wherein the ubenimex is administered orally, intranasally, rectally, topically, intraperitoneally, intravenously, intramuscularly, subcutaneously, subdermally, transdermally, or intrathecally.

19. The method of claim 10, wherein the ubenimex is administered once daily, twice daily, or three times daily.

20. A method of delaying or preventing the progression of non-alcoholic steatohepatitis (NASH) to hepatocellular carcinoma (HCC) in a subject having NASH, the method comprising administering to the subject a therapeutically effective amount of ubenimex.

21. The method of claim 20, wherein the method results in a reduction in hepatocyte ballooning in the subject.

22. The method of claim 20, wherein the ubenimex is administered at a daily dose in the range of 5 mg to 1000 mg.

23. The method of claim 20, wherein the ubenimex is administered at a daily dose of about 5 mg to about 450 mg.

24. The method of claim 23, wherein the ubenimex is administered at a dose of about 20 mg to about 450 mg QD.

25. The method of claim 23, wherein the ubenimex is administered at a dose of about 10 mg to about 200 mg BID.

26. The method of claim 23, wherein the ubenimex is administered at a dose of about 10 mg to about 150 mg TID.

27. The method of claim 20, wherein the ubenimex is administered for at least 4 weeks.

28. The method of claim 27, wherein the ubenimex is administered for at least 12 weeks.

29. The method of claim 20, wherein the ubenimex is administered orally, intranasally, rectally, topically, intraperitoneally, intravenously, intramuscularly, subcutaneously, subdermally, transdermally, or intrathecally.

30. The method of claim 20, wherein the ubenimex is administered once daily, twice daily, or three times daily.

31. A method of treating non-alcoholic steatohepatitis (NASH), the method comprising administering to a subject in need of treatment a therapeutically effective amount of ubenimex, wherein the ubenimex is administered orally, intranasally, rectally, topically, intraperitoneally, intravenously, intramuscularly, subcutaneously, subdermally, transdermally, or intrathecally.

32. The method of claim 31, wherein the subject has early-stage or middle-stage NASH.

33. The method of claim 31, wherein the ubenimex is administered for at least 12 weeks.

34. The method of claim 31, wherein the ubenimex is administered for at least 24 weeks.

35. The method of claim 31, wherein the ubenimex is administered at a total daily dose in the range of 5 mg to 1000 mg.

36. The method of claim 31, wherein treatment results in a reduction in plasma CK-18 levels in the subject.

37. The method of claim 31, wherein treatment results in a reduction in hepatocyte ballooning in the subject.

38. The method of claim 31, wherein the ubenimex is administered in combination with a second therapeutic agent.

39. The method of claim 31, wherein the ubenimex is administered once daily, twice daily, or three times daily.

40. A method of treating non-alcoholic steatohepatitis (NASH), the method comprising administering to a subject in need of treatment a therapeutically effective amount of ubenimex, wherein the ubenimex is administered once daily, twice daily, or three times daily.

41. The method of claim 40, wherein the subject has early-stage or middle-stage NASH.

42. The method of claim 40, wherein the ubenimex is administered for at least 12 weeks.

43. The method of claim 40, wherein the ubenimex is administered for at least 24 weeks.

44. The method of claim 40, wherein the ubenimex is administered at a total daily dose in the range of 5 mg to 1000 mg.

45. The method of claim 40, wherein treatment results in a reduction in plasma CK-18 levels in the subject.

46. The method of claim 40, wherein treatment results in a reduction in hepatocyte ballooning in the subject.

47. The method of claim 40, wherein the ubenimex is administered in combination with a second therapeutic agent.

48. The method of claim 40, wherein the ubenimex is administered orally, intranasally, rectally, topically, intraperitoneally, intravenously, intramuscularly, subcutaneously, subdermally, transdermally, or intrathecally.

* * * * *